US008138162B2

(12) United States Patent
Kannar et al.

(10) Patent No.: US 8,138,162 B2
(45) Date of Patent: Mar. 20, 2012

(54) NATURAL SWEETENER

(75) Inventors: David Kannar, Belgrave South (AU); Barry James Kitchen, Bon Beach (AU)

(73) Assignee: Horizon Science Pty Ltd., Victoria (AU)

( * ) Notice: Subject to any disclaimer, the term of this patent is extended or adjusted under 35 U.S.C. 154(b) by 832 days.

(21) Appl. No.: 11/628,151

(22) PCT Filed: Jun. 3, 2005

(86) PCT No.: PCT/AU2005/000798
§ 371 (c)(1),
(2), (4) Date: Dec. 27, 2006

(87) PCT Pub. No.: WO2005/117608
PCT Pub. Date: Dec. 15, 2005

(65) Prior Publication Data
US 2008/0045464 A1     Feb. 21, 2008

(30) Foreign Application Priority Data

Jun. 4, 2004 (AU) ................................. 2004902997
Apr. 12, 2005 (AU) ................................. 2005901825

(51) Int. Cl.
*A61K 31/715* (2006.01)
*A23L 1/08* (2006.01)
*C13K 1/04* (2006.01)
*C13K 13/00* (2006.01)

(52) U.S. Cl. .............. 514/53; 426/48; 426/103; 127/42; 536/123.13

(58) Field of Classification Search ............... 514/53; 426/48, 103; 536/123.13; 127/42
See application file for complete search history.

(56) References Cited

U.S. PATENT DOCUMENTS

| | | | |
|---|---|---|---|
| 2,170,713 A * | 8/1939 | Fattinger | ..................... 426/635 |
| 3,975,205 A | 8/1976 | Munir et al. | |
| 4,101,338 A | 7/1978 | Rapaport et al. | |
| 4,111,714 A | 9/1978 | Hippchen et al. | |
| 4,116,712 A | 9/1978 | Othmer | |
| 4,333,770 A | 6/1982 | Neuzil et al. | |
| 4,359,430 A | 11/1982 | Heikkila et al. | |
| 4,404,037 A | 9/1983 | Broughton | |
| 4,523,959 A | 6/1985 | Exertier | |
| 4,523,999 A | 6/1985 | Toyoshi et al. | |
| 5,096,594 A | 3/1992 | Rabinowitz | |
| 5,127,957 A | 7/1992 | Heikkila et al. | |
| 5,252,136 A | 10/1993 | Desforges et al. | |
| 5,382,294 A | 1/1995 | Rimedio et al. | |
| 5,384,035 A | 1/1995 | Smolnik et al. | |
| 5,482,631 A | 1/1996 | Saska et al. | |
| 5,556,546 A | 9/1996 | Tanimura et al. | |
| 5,663,156 A | 9/1997 | Granja et al. | |
| 6,093,326 A | 7/2000 | Heikkila et al. | |
| 6,099,654 A | 8/2000 | Kaneko et al. | |
| 6,217,664 B1 | 4/2001 | Baniel | |
| 6,406,547 B1 | 6/2002 | Donovan et al. | |
| 6,406,548 B1 | 6/2002 | Donovan et al. | |
| 6,475,390 B1 | 11/2002 | Durham et al. | |
| 6,528,099 B1 | 3/2003 | Garti et al. | |
| 6,723,369 B2 * | 4/2004 | Burgess | .................. 426/597 |
| 6,869,625 B2 | 3/2005 | Gupta et al. | |
| 7,015,339 B2 | 3/2006 | Khare et al. | |
| 7,312,199 B2 | 12/2007 | Burdick et al. | |
| 2001/0001956 A1 | 5/2001 | Hyoky et al. | |
| 2002/0150652 A1 | 10/2002 | Antila et al. | |
| 2002/0169311 A1 | 11/2002 | Paananen et al. | |
| 2002/0187219 A1 * | 12/2002 | Yang et al. | ..................... 426/72 |
| 2003/0082287 A1 * | 5/2003 | Wolt et al. | ..................... 426/549 |
| 2003/0124170 A1 | 7/2003 | Gallaher et al. | |
| 2003/0124208 A1 | 7/2003 | Makino et al. | |
| 2003/0161903 A1 | 8/2003 | Konishi et al. | |
| 2003/0165574 A1 | 9/2003 | Ward et al. | |
| 2003/0198694 A1 | 10/2003 | Chou | |
| 2003/0232763 A1 | 12/2003 | Jia | |
| 2004/0001862 A1 | 1/2004 | Xiu | |
| 2004/0006222 A1 | 1/2004 | Paananen et al. | |
| 2004/0006223 A1 | 1/2004 | Karki et al. | |
| 2004/0060868 A1 | 4/2004 | Heikkila et al. | |
| 2004/0081734 A1 | 4/2004 | Lang | |
| 2004/0097429 A1 | 5/2004 | Nieuwenhuizen et al. | |
| 2004/0131749 A1 | 7/2004 | Grabiel et al. | |
| 2004/0151815 A1 | 8/2004 | Jensen et al. | |
| 2004/0191336 A1 | 9/2004 | Hilaly et al. | |
| 2004/0197380 A1 | 10/2004 | Wolf et al. | |
| 2005/0175674 A1 | 8/2005 | Lang et al. | |
| 2005/0181074 A1 | 8/2005 | Watson et al. | |

(Continued)

FOREIGN PATENT DOCUMENTS

CA           2053412           4/1992

(Continued)

OTHER PUBLICATIONS

Brochure, Queensland Sugar Corporation, "Sugar Notes", Jul. 1997.
Aijun, Dong et al., "A Functional Oligosaccharide in Sugar Beet—Raffinose," China Beet & Sugar, No. 3, Sep. 2001, pp. 24-26.
Yinfa, Zhang et al., "Application of Food Glycemic Index in Diabetes Nutrition Education," Acta Nutrimenta Sinica, Sep. 2003, vol. 25, No. 3, pp. 248-251.
Yoshikawa M. et al., "Medicinal Foodstuffs. III. Sugar Beet. (1): Hypoglycemic Oleanolic Acid Oligoglycosides, Betavulgarosides, I, II, III and IV from the Roota of Beta Vulgaris L. (Chenopodiacae),"
*Chemical and Pharmaceutical Bulletin*, Pharmaceutical Society of Japan, Tokyo, JP, vol. 44, No. 6, Jan. 1, 1996, p. 1212-1217.
European Search Resport for EP appln. 05744686.6-2114 (DatedJun. 26, 2009).
Altukhov et al., 2004, Human Physiol. 30(2):216-223.
Anderson, 2008, Proc. Nutrition Soc. 67:48-53.
Baba et al., 2005, Eur. J. Nutr. 44:1-9.
Badescu et al., 2005, Rom. J. Physiol. 42:1-4.
Balasubramanian et al., 2010, Carcinogenesis 31(3):496-503.
Banini et al., 2006, Nutrition 22:1137-1145.

(Continued)

*Primary Examiner* — Shaojia Anna Jiang
*Assistant Examiner* — Everett White
(74) *Attorney, Agent, or Firm* — Dilworth Paxson LLP; Gary D. Colby

(57) ABSTRACT

The invention relates to extracts, in particular non-nutrient phytochemicals, form sugar cane or sugar beet waste products, such as molasses, sugar mud and bagasse, which have Glycemic Index (GI) lowering properties and their use as sweeteners and in foods containing sugar.

12 Claims, 9 Drawing Sheets

U.S. PATENT DOCUMENTS

| | | | |
|---|---|---|---|
| 2006/0003029 A1 | 1/2006 | Nash et al. |
| 2006/0121158 A1 | 6/2006 | Ferruzzi et al. |
| 2006/0147556 A1 | 7/2006 | Brewer |
| 2007/0158269 A1 | 7/2007 | Paananen et al. |
| 2007/0160698 A1 | 7/2007 | Waga et al. |
| 2007/0178175 A1 | 8/2007 | Matsubara et al. |
| 2008/0286254 A1 | 11/2008 | Sakamoto et al. |
| 2009/0047368 A1 | 2/2009 | Numata et al. |
| 2009/0053333 A1 | 2/2009 | Sambanthamurthi et al. |
| 2009/0281057 A1 | 11/2009 | Bhaskaran et al. |
| 2010/0112099 A1 | 5/2010 | Tripp et al. |
| 2010/0130422 A1 | 5/2010 | Bernaert et al. |
| 2010/0166851 A1 | 7/2010 | Dallas |
| 2010/0184666 A1 | 7/2010 | Bernaert et al. |

FOREIGN PATENT DOCUMENTS

| | | |
|---|---|---|
| CA | 2 420 881 | 9/2001 |
| CN | 1484974 | 3/2004 |
| CN | 1685929 | 10/2005 |
| CN | 101317850 | 12/2008 |
| EP | 1362517 A | 11/2003 |
| EP | 1362919 A | 11/2003 |
| EP | 1447013 A | 8/2004 |
| EP | 1447014 A | 8/2004 |
| EP | 1466609 | 10/2004 |
| JP | 59 020223 A | 2/1984 |
| JP | 61 069727 A | 4/1986 |
| JP | 61 083130 A | 4/1986 |
| JP | 61-265068 | 11/1986 |
| JP | 62-126951 | 6/1987 |
| JP | 03-145424 | 6/1991 |
| JP | 03 145424 A | 6/1991 |
| JP | 04-320691 | 11/1992 |
| JP | 05-211900 | 8/1993 |
| JP | 06 062798 A | 3/1994 |
| JP | 60 062798 A | 3/1994 |
| JP | 61-69727 | 6/1994 |
| JP | 08 040912 A | 2/1996 |
| JP | 11-075758 | 3/1999 |
| JP | 2001-131080 | 5/2001 |
| JP | 2002-020306 | 1/2002 |
| JP | 2003 116486 A | 4/2003 |
| JP | 2003137803 A | 5/2003 |
| JP | 2005-278407 | 10/2005 |
| JP | 2006-131578 | 5/2006 |
| JP | 2006-321772 | 11/2006 |
| JP | 2007-043940 | 2/2007 |
| JP | 2007-063221 | 3/2007 |
| JP | 2008-044872 | 2/2008 |
| JP | 2008-222656 | 9/2008 |
| JP | 09-025290 | 2/2009 |
| JP | 2009-298769 | 12/2009 |
| RU | 2048847 | 11/1995 |
| WO | WO 94/12057 | 6/1994 |
| WO | WO 01/78629 | 10/2001 |
| WO | WO 02/14477 | 2/2002 |
| WO | WO 02/078469 A1 * | 10/2002 |
| WO | 03/074144 | 9/2003 |
| WO | WO 03/074145 | 9/2003 |
| WO | 2004/014159 A1 | 2/2004 |
| WO | 2005/006891 A1 | 1/2005 |
| WO | WO 2005/052195 | 6/2005 |
| WO | WO 2005/089066 | 9/2005 |
| WO | WO 2005/105852 | 11/2005 |
| WO | WO 2006/014028 | 2/2006 |
| WO | WO 2006/052007 | 5/2006 |
| WO | WO 2007/041817 | 4/2007 |
| WO | WO 2008/142178 | 11/2008 |
| WO | WO 2009/046492 | 4/2009 |
| WO | WO 2009/136219 | 11/2009 |
| WO | WO 2010/094860 | 8/2010 |
| WO | WO 2010/118474 | 10/2010 |

OTHER PUBLICATIONS

Basu et al., 2010, J. Nutr. 140:1582-1587.
Bento et al., 1998, Carbohydrate Polymers 37:257-261.
Bento et al., 1997, Intl. Sugar J. 99(1187 Suppl.):555-562.
Bento et al., 1997, SIT Poster #722 Publ. Techn. Papers Proc. Ann. Meet. Sugar Industry Technologiests 56:383-392 "Gel Permeation Chromatography of Sugar Materials Using . . . ".
Berhow et al., 2000, Mutation Res. 448:11-22.
Brown et al., 2009, Br. J. Nutr. 101:886-894.
Burkon et al., 2008, Mal. Nutr. Food Res. 52:549-557.
Chajuss, 2004, "Soy Molasses: Processing and Utilization as a Functional Food," In: Soybeans as Functional Foods and Ingredients, Liu et al., Eds.
Clarke et al., "Polyfructose: A New Microbial Polysaccharide," In: Carbohydrates as Organic Raw Materials, Lichtenthaler, Ed., VCH, Weinheim, 1990.
Coca et al., 2005, Chemosphere 60:1408-1415.
Dal-Pan et al., 2010, BMC Physiol. 10:11.
Dallas et al., 2008, Phytomedicine 15:783-792.
Edye et al., 1998, "The Fate of Soluble Sugarcane Polysaccharides in Sugar Manufacture," Poster.
Fernandes et al., 2009, Talanta 79:222-228.
Frank et al., 2009, J. Nutr. 139:58-62.
Fujita et al., 2000, Abstract AGFD-086, Book of Abstracts, 219th ACS National Meeting, San Francisco, CA, Amer. Chem. Soc., Washington, DC.
Fukino et al., 2008, Eur. J. Clin. Nutr. 62:953-960.
Fukino et al., 2005, J. Nutr. Sci. Vitaminol. 51:335-342.
Hangyal, 1969, Cukoripar 22(5):183-186 (Abstract only; HCAPLUS database record No. 1970:123241).
Hatano et al., 2008, Chemosphere 71:1730-1737.
Hollis et al., 2009, J. Amer. Coll. Nutr. 28(5):574-582.
Islam, 2008, Z. Naturforsch. 63c:233-240.
Jacome et al., 2009, Alim. Nutr. 20(2):185-190.
Kantachote, 2009, Electr. J. Biotechnol. 12(3):12.
Khan et al., 2010, 61(15):4185-4196.
Kita et al., 2004, BioFactors 22:259-263.
Kovacs et al., 2004, Br. J. Nutr. 91:431-437.
Loke et al., 2010, Arterioscler. Thromb. Vasc. Biol. 30:749-757.
Machowetz et al., 2008, Horm. Metab. Res. 40:697-701.
Mantovani et al., 2008, Nutrition 24:305-313.
Mantovani et al., 2006, Cancer Epidemiol. Biomarkers Prev. 15:1030-1034.
Mantovani et al., 2004, Cancer Epidemiol. Biomarkers Prev. 13 (10):1651-1659.
Nagasako-Akazome et al., 2007, J. Oleo Sci. 56(8):417-428.
Ochiai et al., 2009, Hypertension Res. 32:969-974.
Olthof et al., 2000, "Metabolism of Chlorogenic Acid, Quercetin-3-rutinoside and . . . " In: Spec. Publ. Royal Soc. Chem: 255 Dietary Anticarcinogens and Antimutagens, pp. 73-75.
Onimawo et al., 2010, African J. Food Agric. Nutr. Develop. 10(5).
Palfi et al., 2009, J. Nutr. Biochem. 20:418-425.
Pena et al., 2003, Chemosphere 51:893-900.
Schoen et al., 2009, Nutrition 25:499-505.
Shore et al., 1984, Sugar Technol. Rev. 12:1-99.
Simonetti et al., 2001, Meth. Enzymol. 335:122-130.
Stracke et al., 2010, Eur. J. Nutr. 49:301-310.
Tominaga et al., 2006, J. Health Sci. 52(6):672-683.
Vercellotti et al., 1998, Membrane Separation Chemistry in Sugar Processing Applications, Proceedings of the Conference on Sugar Processing Research, Savannah, GA, pp. 248-228.
Vercellotti et al., 1998, SIT Paper 727, Sugar Industry Technologist Annual Meeting, Marseille France, pp. 49-78.
Vercellotti et al., 1996, Proc. Conf. Sugar Processing Res., SPRI, New Orleans, 321-349.
Wachowicz, 1978, Gazeta Cukrownicza 86:125-127 (Abstract Only; HCAPLUS database record No. 1978:548469).
Wang et al., 2008, Carbohydrate Polymers 74:127-132.
Winter et al., 1992, J. Exp. Mar. Biol. Ecol., 155:263-277.
Wu et al., 2005, Carcinogenesis 26(5):976-980.
Zhang et al., 2007, Can. J. Physiol. Pharmacol. 85:1116-1123.
Zielinska-Przyjmeska et al., 2007 Acta Sci. Pol., Technol. Aliment. 6 (3):75-87.
Zhang et al., 2009, Zhongguo Difangbingxue Zazhi 28(4):381-385 (Abstract Only).
Nagao et al., 2009, Jap. Pharmacol. Therapeut. 37(4):333-344 (Abstract Only).

Ishikura et al., 2008, Jap. Pharmacol. Therapeut. 36(10):931-939 (Abstract Only).
Lee et al., 2008, Hanguk Kikpum Yongyang Kwahak Hoechi 37(5):561-570 (Abstract Only).
Nakamura et al., 2008, Jap. Pharmacol. Therapeut. 36(4):347-357 (Abstract Only).
Hu et al., 2006, Zhongguo Linchuang Kangfu 10(43):79-81 (Abstract Only).
Melby et al., 2007, Daizu Tanpakushitsu Kenkyu 9:138-146 (Abstract Only).
Nakamura et al., 2007, Jap. Pharmacol. Therapeut. 35(6):661-671 (Abstract Only).
Zielinska-Przyjemska et al., 2005, Polski Merkuriusz 19(109):41-47 (Abstract Only).
Kishihara et al., 1986, Kagaku Kogaku Ronbunshu 12(2):199-205 (Abstract Only).
Bray et al., 1999, Endocrine Rev 20(6):805-875.
Goossens et al., 2003, Obesity Rev. 4:43-55.
Kumar et al., 1998, Indian Vet. Med. J. 22:185-188.
Rosenberg et al., 1956, "Response of Growing and Mature Pullets to Continuous Feeding of Cane Final Molasses," Hawaii Agricultural Experiment Station Technical Paper No. 349.
Zheng et al., 2004, In Vivo 18:55-62.
Mehra et al., 1998, Asian-Australasian J. Animal Sci.11 (1):30-34.
Zemel, 2002, J. Am. Coll. Nutr. 21(2):146S-151S.
Han et al., 2003, Phytother. Res. 17:1188-1194.
Kajimoto et al., 2005, J. Health Sci. 51(2)161-171.

* cited by examiner

NATURAL SWEETENER

FIELD OF THE INVENTION

The invention relates to non-nutrient phytochemicals having desirable properties and health benefits. More particularly the invention relates to non-nutrient phytochemicals which lower the glycemic index of foods such as sugar. The invention also relates to an improved sweetener. More particularly, the invention also relates to a sucrose product comprising added non-nutrient phytochemicals and having a lower glycemic index.

BACKGROUND OF THE INVENTION

In this specification, where a document, act or item of knowledge is referred to or discussed, this reference or discussion is not to be taken as an admission that the document, act or item of knowledge was at the priority date (i) part of common general knowledge; or (ii) known to be relevant to an attempt to solve any problem with which this specification is concerned.

Fundamentals of Good Health and Nutrition

Nutrition is usually considered from the perspective of the relationship between food and human health. Good nutrition:
- involves ensuring that all the essential nutrients are adequately supplied and utilized to optimize health and well being;
- is essential to growth, reproduction and maintenance of normal body function; and
- is also essential for optimal activity, resistance to infection and repair of damage or injury.

Until recently, nutritionists have focused primarily on the nutrient elements in foods. Nutrients in foods have historically been classified into macronutrients (protein, carbohydrate, fat) and micronutrients (vitamins, minerals, water and essential elements). However, food is also composed of non-nutrient factors or phytochemicals, which are now thought to have their own beneficial effects, such as reducing the risk of cancer or heart disease.

No single substance is sufficient to maintain adequate health. For this reason, a variety of foods are needed in a diet to assist with delivery of a broad array of micronutrients, macronutrients and non-nutrient plant components (also known as phytochemicals). Some specific nutrients are known to be singly effective, eg fibre, however, most nutrients work more effectively when combined with other dietary components and the body's own chemical products, enzymes and co-factors, to enable absorption and utilization. Phytochemicals (substances found in plants) are important components of food that are likely to be essential for optimal health. The main classes of phytochemicals found in fruit and vegetables include plant sterols, flavonoids and sulfur-containing compounds. Nutritional science has begun to focus more on the role of specific foods and food phytochemicals in reducing the risk of diseases such as obesity, diabetes, arthritis and other chronic non infectious diseases such as osteoporosis, high blood pressure, high blood cholesterol, cancer and health problems like migraine and menopausal symptoms. Examples of phytochemicals and their postulated health benefits are as follows

- Anthocyanins/Proanthocyanidins are found in berries, cherries, red grapes, plums and red-cabbage and are thought to protect the heart, lungs and blood vessels.
- Bioflavonoids (e.g., Taxifolin, Rutin, Ellagic Acid, Quercetin) are found in citrus fruits, black tea, red wine, onions, tomatoes, apples, potatoes, grapes and broad beans and are thought to be an antioxidant and have anti-cancer benefits.
- Carotenoids (eg. Lycopene, Lutein, Capsanthin) are found in carrots, mangos, peaches, pumpkin, squash, sweet potatoes, tomatoes and dark leafy green vegetables and are thought to have anti-cancer benefits.
- Catechins (eg. Epigallocatechin Gallate) are found in green tea and apples and are thought to be antioxidants and have anti-cancer benefits.
- Glucosinolates (eg. Sulphoraphane Sinigrin Isothiocyanate) are found in broccoli, brussel sprouts, cabbage, kale and watercress and are thought to have anti-cancer properties including the ability to reduce the growth of pre-cancerous cells.
- Organosulphides (eg. Allicin) are found in garlic, onions and leeks and are thought to help fight stomach cancer and reduce LDL cholesterol.
- Phytoestrogens (eg. Isoflavones, Lignans) are found in soy beans, flax seeds and berries and are thought to protect against breast cancer, prostate cancer and menopause symptoms
- Bromelain is found in pineapples and is thought to have blood-thinning properties.
- Capsaicin is found in chilies and is thought to be an antioxidant and pain-reliever.
- Chlorophyll is found in wheat grass, seaweeds and dark green vegetables and is thought to have anti-cancer and antiradiation properties.
- Coumarins are found in tomatoes, green peppers, strawberries and carrots and are thought to have blood-thinning benefits.
- Papain is found in papaya and is thought to help relieve pain.
- Resveratrol is found in red grapes and is thought to help protect against heart disease.

US patent application no 2003198694 teaches that antioxidant compounds can be extracted from natural sugar cane and beet which can be used in the production of functional food products. The antioxidant compounds disclosed by the inventors include polyphenols and flavonoids.

Glycemic Index

The glycemic index (GI), invented in 1981 by David Jenkins and Thomas Wolever of the University of Toronto, is a new system for classifying carbohydrate-containing foods, according to how fast they raise blood-glucose levels inside the body. In simple terms, a food with a higher GI value raises blood glucose faster and is less beneficial to blood-sugar control than a food which scores lower.

The GI consists of a scale from 1 to 100, indicating the rate at which 50 grams of carbohydrate in a particular food is absorbed into the bloodstream as blood-sugar. Glucose itself is used as the main reference point and is rated 100.

The GI separates carbohydrate-containing foods into three general categories:
- High Glycemic Index Foods (GI 70+) causing a rapid rise in blood-glucose levels;
- Intermediate/Medium Glycemic Index Foods (GI 55-69) causing a medium rise in blood-glucose; and
- Low Glycemic Index Foods (GI 54 or less) causing a slower rise in blood-sugar.

The glycemic load (GL) ranks foods according to actual carbohydrate content and indicates how much carbohydrate is in a standard serving size of food. To calculate glycemic load in a typical serving of food, divide the GI of that food by 100 and multiply this by the useable carbohydrate content (in grams) in the serving size. For example, the glycemic index of carrots is about 47. Carrots contain about 7 grams of carbohydrate per 100 g of carrots. So, to calculate the glycemic load for a standard 50 g serving of carrots, divide 47 by 100 (0.47) and multiply by 3.5. The glycemic load of carrots is therefore 1.6. Several factors influence how fast a particular carbohydrate food raises blood sugar. These factors include: the chemical and physical structure of the carbohydrate-food in question; how refined the carbohydrate is; how the carbohydrate is cooked; and also the presence of other substances which reduce either the potency of the body's digestive enzymes, or the speed of digestion. Each of these factors is discussed further below.

Chemical structure of the carbohydrate: For example, the body processes glucose very efficiently, but the body cannot easily metabolize fructose, a common monosaccharide in fruits, which is why fructose has a low GI of 23. Ordinary table sugar (sucrose), is a disaccharide made up of one molecule of glucose linked to one of fructose. Hence the glycemic index of table sugar is 65, midway between 23 and 100 in the medium-glycemic-index range.

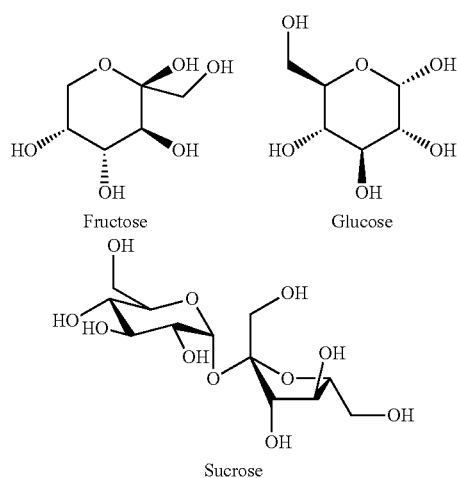

Physical structure of the carbohydrate: For example, most breads are in the high range—not due to the chemical nature of wheat starch, but for two physical reasons. (1) The fine particle size of wheat flour gives digestive enzymes great surface area to attack and metabolize the bread. (2) The surface area of bread is also increased by its puffed-out, fluffy structure. The glycemic value of bread is significantly raised by these structural attributes.

Level to which the carbohydrate is refined: One of the most important factors that determines the GI of carbohydrate foods is how refined or processed are the carbohydrates. In general, refined or processed carbohydrates have had most of their 'natural' fiber and other 'inconvenient' constituents (eg. which may affect the food's shelf-life) removed. The carbohydrate is incapable of resisting the digestive enzymes and is rapidly metabolized into glucose.

Extent to which the carbohydrates are cooked or prepared: Pasta has a medium-GI value of 40-50. This can be further reduced by cooking it less (al dente). This is because al dente pasta resists the effect of digestive enzymes more than regular cooked pasta and so has a lower GI.

Fiber slows down metabolism and digestion of carbohydrates: Fiber (either in the carbohydrate itself or in the stomach) protects the starchy carbohydrate from rapid attack by digestive enzymes, or slows digestion in the digestive tract. Either of these consequences will slow down the conversion of the carbohydrate to glucose.

Fat and/or acid slows down metabolism and digestion of carbohydrates: The more fat or acid a carbohydrate food contains, (or the more fat or acid in the stomach during digestion) the slower the carbohydrate food is converted to glucose and absorbed into the bloodstream. The presence of fat and/or acid retards the emptying of the stomach. An increase in acid can be achieved by adding vinegar or lemon juice to the diet.

The GI of many foods has been assessed. Honey has a broad GI depending upon the type. Romanian locust honey for example has a GI of 32 whereas Canadian honey has a GI of 87. Foods containing longer chain carbohydrates-fructo-oligosaccharides such as Jerusalem artichokes have a GI of 0. Fruits also contain carbohydrates but some are low GI and some are high GI. Apples have a GI of 38 and watermelon 72.

Issues Raised by High GI Diets Include the Following.

High-glycemic-index foods trigger strong insulin responses, thereby exposing the body to all the negative effects of insulin. By comparison, low-glycemic value foods do not provoke this insulin response.

Diets containing high-glycemic-index meals, which cause rapid and strong increases in blood-sugar levels, have been linked to an increased risk for diabetes.

Over-consumption of high-glycemic-index carbohydrates may aggravate insulin resistance in patients predisposed to the condition. Insulin resistance (called Metabolic Syndrome X, or more properly, Insulin Resistance Syndrome) is believed to be a precursor of type II diabetes.

Insulin resistance is believed to be a genetic condition, aggravated by obesity. However, some experts consider that it may be the result of a separate inherited sensitivity to high-glycemic-index carbohydrates.

Lower glycemic index diets have been shown to help control type II diabetes and reduce symptoms of insulin resistance.

High-glycemic-index diets have also been linked to an increased risk for heart disease.

Over-consumption of high-glycemic-index foods has also been linked to food cravings and disordered eating patterns as a result of repeated surges and falls in blood-glucose ("sugar spikes").

Low GI Diets

It is now thought that individuals who are susceptible to type II diabetes and coronary heart disease should follow a low GI diet. It has also been found that following a low GI diet can assist individuals with diabetes to manage their sugar levels and it can assist individuals with obesity problems to control food cravings, reduce appetite swings and improve eating habits.

One example of an attempt to lower the GI of foods is disclosed in international patent application no WO2004/014159. The method disclosed involves administering an effective amount of flavonoids which inhibit the action of the enzymes (eg α-amylase) which break down carbohydrate in the intestine, thereby inhibiting the rate at which glucose is released into the bloodstream.

Sugar

Sugar is a common carbohydrate used in food because of its sweet taste.

After being mechanically harvested, sugar cane is transported to a mill and crushed between serrated rollers. The crushed sugar cane is then pressed to extract the raw sugar juice, while the bagasse (leftover fibrous material) is used for fuel. The raw juice is then heated to its boiling point to extract any impurities and lime and bleaching agents are added and mill mud is removed. The raw juice is further heated under vacuum to produce bulk sugar crystals and a thick syrup known as molasses. The two are separated by a centrifuge and the molasses waste stream is collected for use as a low-grade animal feedstock. The bulk sugar crystals are further refined to increase their purity.

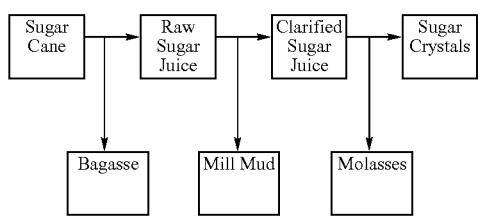

The bulk sugar crystals from the above process are further refined to produce the many commercially available sugar products. The bulk sugar crystals are mixed with a hot concentrated syrup to soften the outer coating on the crystals. The crystals are recovered by centrifuge and then dissolved in hot water. This sugar liquor is then further purified by carbonation or phosfloatation, filtration, decolourisation and then seeded with fine sugar crystals. Once the crystals have grown to the requisite size, the crystals are separated from the syrup by centrifuge, dried, graded and then packaged. There may be several repetitions of recovering sugar crystals from the sugar liquor. The dark sugar syrup which is left after all of the sugar crystals have been recovered is also called molasses.

Almost all of the commercially manufactured sugar is white and granulated. White graded sugar is 99.5% sucrose and is made up of crystals averaging 0.6 mm. Caster sugar has an average crystal size of 0.3 mm. Icing sugar is produced by crushing white sugar in a special mill to produce a fine powder.

There are also a range of non-white sugar products. Coffee sugar is a large grained, brown flavoursome crystal which is produced using the syrups left after extracting the white sugar crystals. Raw sugar is a straw-coloured granulated sugar produced from sucrose syrups which contain some residual colour and flavour from the sugar cane plant—it is specially selected and handled to ensure a hygienic product. Golden demerara sugar is a premium raw sugar produced from selected syrups which imparts a rich caramel taste to food. Brown sugar is a flavoursome, fine-grained and moist crystal produced by further crystallization of the extracted dark coloured sucrose syrups produced in the separation stages of the refining process.

The syrup left after white sugar has been removed is used to make golden syrup and treacle. These syrups are made in a similar fashion with the difference being that golden syrup is decolourised whereas treacle is not.

Approximately 70% of the world's sugar comes from sugar cane and about 30% comes from sugar beets. Similar processes are used to manufacture sugar products from sugar beets. However, it is a single step rather than two step process.

The beets are harvested in the autumn and early winter by digging them out of the ground. Because the beets have come from the ground they are much dirtier than sugar cane and have to be thoroughly washed and separated from any remaining beet leaves, stones and other trash material before processing. The processing starts by slicing the beets into thin strips/chips/cossettes. This process increases the surface area of the beet to make it easier to extract the sugar. The extraction takes place in a diffuser where the beet is kept in contact with hot water and the resultant sugar solution is referred to as the juice. The exhausted beet slices from the diffuser are still very wet and the water in them still holds some useful sugar so they are pressed to squeeze as much juice as possible out of them. The pressed beet, by now a pulp, is sent to drying plant where it is turned into pellets which form an important constituent of some animal feeds. The juice is then cleaned up before it can be used for sugar production and the non-sugar chemicals are removed in a process called carbonation (milk of lime (calcium hydroxide) and carbon dioxide gas). The calcium carbonate (chalk) which forms traps the non-sugar chemicals and is removed (called mud) in the clarifier. Once this is done the sugar liquor is concentrated until sugar crystals form. Once the crystals have grown the resulting mixture of crystals and mother liquor is spun in centrifuges to separate the two, rather like washing is spin dried. The crystals are then given a final dry with hot air before being packed and/or stored ready for despatch. The final sugar is white and ready for use. Because one cannot get all the sugar out of the juice, there is a sweet by-product made: beet molasses. This is usually turned into a cattle food or is sent to a fermentation plant such as a distillery where alcohol is made.

Table sugar is 99.5% sucrose, the most biologically abundant disaccharide. Saccharides are simple carbohydrates classified as monosaccharides, oligosaccharides or polysaccharides depending upon their structure. Sucrose consists of glucose and fructose bound by a α-1,2-glycoside bond and is sourced from both sugarcane and beets. As discussed above, sucrose has a GI of about 65.

One of the most difficult dietary changes faced by someone who has to change to a low GI diet is to reduce the amount of sugar which they consume. This is usually achieved by replacing the sugar with artificial sweeteners such as aspartame. However, artificial sweeteners have drawbacks, including their unnatural taste.

Fructose

In an attempt to provide low GI foods, many people started using fructose as a sweetener instead of sucrose/table sugar. As mentioned above, fructose has a low GI of 23 and thus had benefits for diabetics. Fructose is readily available as corn syrup and in addition to use by diabetics it is being used in a variety of food, drink and confectionary around the world. However, there are now concerns that consumption of fructose as a sweetener has detrimental effects including increasing the total serum cholesterol and the level of low density lipoproteins (LDL);

increases in the level of uric acid which is linked to heart disease;

increasing in the level of blood lactic acid which can lead to metabolic acidosis and death, causing the loss of important nutrients minerals such as calcium, phosphorus, magnesium and zinc;

increasing amounts of fat production; and reducing the affinity of insulin for its receptor so that the pancreas is actually induced to produce more insulin that it would need for the same amount of glucose.

Energy dense and low GI foods are recommended for those at risk of diabetes and coronary heart disease. In light of these concerns, there is a need for a low GI sweetener with fewer disadvantages. Sucrose products or sweeteners with low GI index are therefore desirable. There is thus a need for sugar to have its GI reduced so that it is in the low GI range (54 or less) and more acceptable for a low GI diet.

SUMMARY OF THE INVENTION

Figure 1:
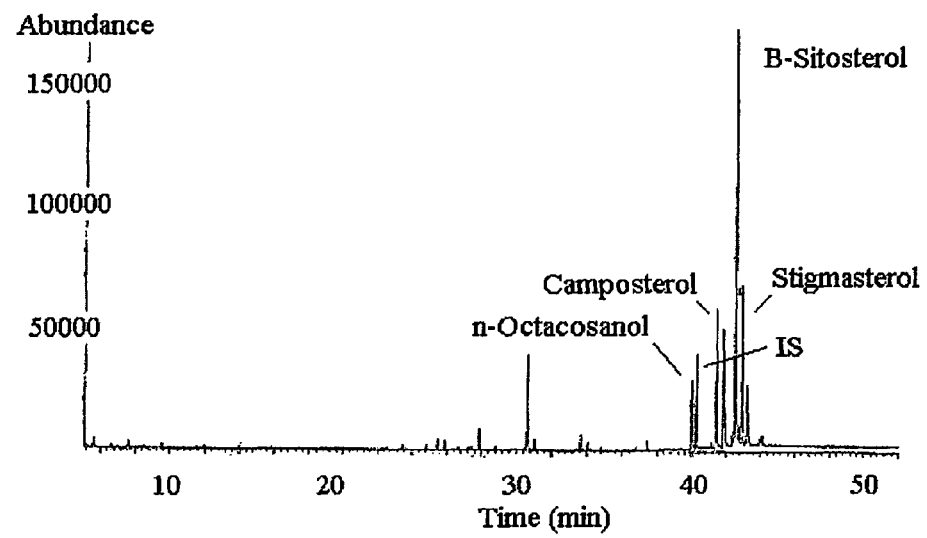
FIG. 1 shows a chromatogram of the extract (after derivation) from sugar cane tops.
Figure 1:
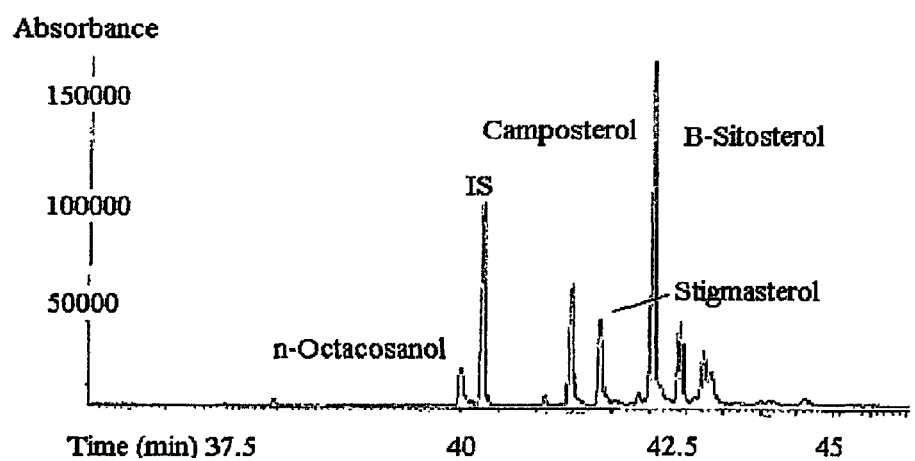

It has now been found that the final waste streams and some in-process products in the sugar manufacturing process contain useful substances which can be used to modify the energy density, burn rate and GI of sugar products and food containing sugar.

According to a first aspect of the invention, there is provided a molasses extract having GI or burn rate reducing characteristics comprising substantially no content of any carbohydrates having GI increasing characteristics.

The molasses extract may contain one or more of the following substances: lipids, phospholipids, protein, flavonoids such as anthocyanins, catechins, chalcones, flavonols and flavones, polyphenols, antioxidants, phytosterols such as 1-octacosanol, campesterol, stigmasterol, β-sitosterol, oligosaccharides such as raffinose, 1-kestose, theanderose, 6-kestose, panose, neo-kestose and nystose, and organic acids such as c-aconitic acid, citric acid, phosphoric acid, gluconic acid, malic acid, t-aconitic acid, succinic acid and lactic acid, aliphatic alcohols, vitamins, minerals, carbohydrates, gums and neutral and polar lipids.

A person skilled in the art will know what carbohydrates have GI increasing characteristics. Typical examples of carbohydrates having GI increasing characteristics are sucrose, glucose, simple polysaccharides and pectins.

According to a second aspect of the invention, there is provided a sugar mud extract having GI or burn rate reducing characteristics comprising substantially no content of any carbohydrates having GI increasing characteristics.

The sugar mud extract may contain one or more of the following substances: lipids, phospholipids, protein, flavonoids such as anthocyanins, catechins, chalcones, flavonols and flavones, polyphenols, antioxidants, phytosterols such as I-octacosanol, campesterol, stigmasterol, β-sitosterol, oligosaccharides such as raffinose, 1-kestose, theanderose, 6-kestose, panose, neo-kestose and nystose, and organic acids such as c-aconitic acid, citric acid, phosphoric acid, gluconic acid, malic acid, t-aconitic acid, succinic acid and lactic acid, aliphatic alcohols, vitamins, minerals, carbohydrates, gums and neutral and polar lipids.

According to a third aspect of the invention, there is provided an extract from the juice and/or foam collected from the clarifying tank having GI or burn rate reducing characteristics comprising substantially no content of any carbohydrates having GI increasing characteristics.

The clarifying tank extract may contain one or more of the following substances: lipids, phospholipids, protein, flavonoids such as anthocyanins, catechins, chalcones, flavonols and flavones, polyphenols, antioxidants, phytosterols such as 1-octacosanol, campesterol, stigmasterol, β-sitosterol, oligosaccharides such as raffinose, 1-kestose, theanderose, 6-kestose, panose, neo-kestose and nystose, and organic acids such as c-aconitic acid, citric acid, phosphoric acid, gluconic acid, malic acid, t-aconitic acid, succinic acid and lactic acid, aliphatic alcohols, vitamins, minerals, carbohydrates, gums and neutral and polar lipids.

According to a fourth aspect of the invention, there is provided an extract from sugar cane or sugar beet field trash/fibrated sugar cane tops having GI or burn rate reducing characteristics comprising substantially no content of any carbohydrates having GI increasing characteristics.

The sugar cane or sugar beet field trash/fibrated sugar cane tops extract may contain one or more of the following substances: lipids, phospholipids, protein, flavonoids such as anthocyanins, catechins, chalcones, flavonols and flavones, polyphenols, antioxidants, phytosterols such as 1-octacosanol, campesterol, stigmasterol, β-sitosterol, oligosaccharides such as raffinose, 1-kestose, theanderose, 6-kestose, panose, neo-kestose and nystose, and organic acids such as c-aconitic acid, citric acid, phosphoric acid, gluconic acid, malic acid, t-aconitic acid, succinic acid and lactic acid, aliphatic alcohols, vitamins, minerals, carbohydrates, gums and neutral and polar lipids.

According to a fifth aspect of the invention, there is provided an extract from bagasse/pulp having GI or burn rate reducing characteristics comprising substantially no content of any carbohydrates having GI increasing characteristics.

The bagasse/pulp extract may contain one or more of the following substances: lipids, phospholipids, protein, flavonoids such as anthocyanins, catechins, chalcones, flavonols and flavones, polyphenols, antioxidants, phytosterols such as 1-octacosanol, campesterol, stigmasterol, β-sitosterol, oligosaccharides such as raffinose, 1-kestose, theanderose, 6-kestose, panose, neo-kestose and nystose, and organic acids such as c-aconitic acid, citric acid, phosphoric acid, gluconic acid, malic acid, t-aconitic acid, succinic acid and lactic acid, aliphatic alcohols, vitamins, minerals, carbohydrates, gums and neutral and polar lipids.

As used herein, the term "molasses" refers to the dark syrup which is left behind after the bulk sugar crystals are collected in the sugar cane mill, the black syrup remaining after the sugar cane syrup has been centrifuged for the last time in the refinery or beet molasses. Preferably, the molasses used is from the sugar cane mill.

As used herein, the term "sugar mud" refers to the dense substance collected as waste during the clarification of the sugar cane juice in the sugar cane mill or the calcium carbonate mixture collected during clarification of sugar beet juice.

As used herein, the term "juice or foam from the clarifying tank" refers to the in-process product comprising the lighter substances collected during the clarification of the sugar cane juice in the sugar cane mill.

As used herein, the term "field trash/fibrated sugar cane tops" refers to the material collected as waste after harvesting. In particular, field trash refers to waste from harvesting either sugar cane or sugar beets.

As used herein, the term "bagasse" refers to the left over fibrous material after the raw sugar cane juice has been extracted. As used herein, the term "pulp" refers to the material left after the sugar beet juice has been collected.

As used herein, the term "in-process products" in the sugar manufacturing process refers to stages of the sugar refining process where the product is substantially less refined. For example, the juice or foam from the clarifying tank and the sugar syrup obtained from the sugar beets are in-process products.

As used herein, "substantially no content of any carbohydrates having GI increasing characteristics" refers to a composition wherein the amount of GI increasing carbohydrates does not inhibit the GI lowering effects of the extract. A person skilled in the art will know that if the extract contains more GI increasing carbohydrates then the extract will need to contain more GI lowering components. Preferably, the extract has no more than 2% of GI increasing carbohydrates. More preferably, there is no more than 1.5%.

According to a sixth aspect of the invention, there is provided a method for extracting non-nutrient phytochemicals having GI or burn rate reducing properties from sugar processing waste streams and other in-process products such as juice or foam from the clarifying tank, molasses, mill mud, pulp and bagasse the method comprising the following steps:

extracting non-nutrient phytochemicals from the sugar processing waste streams and other in-process products using an aqueous solvent;

filtering the extracted non-nutrient phytochemicals to remove particulate matter;

separating the low and high molecular weight components by size exclusion processing using either gel permeation chromatography or ultrafiltration;

optionally, separating the low and high molecular weight components using ion exchange and/or a combination of hydrophobic chromatography; and recovering the extracted non-nutrient phytochemicals.

Pure fractions of components are recovered and can be concentrated by microfiltration, reverse osmosis, vacuum evaporation and freeze drying.

The small molecular weight components include, but are not limited to, mono and disaccharides, anions, cations, organic and amino acids, and peptides. The large molecular weight components include, but are not limited to, oligo and polysaccharides, proteins, polyphenols and other phytochemicals.

In another embodiment, the method for extracting non-nutrient phytochemicals having GI or burn rate reducing properties from sugar processing waste streams and other in-process products such as juice or foam from the clarifying tank, molasses, mill mud, and bagasse the method comprising the following steps:

extracting non-nutrient phytochemicals from the sugar processing waste streams and other in-process products using an aqueous solvent;

filtering the extracted non-nutrient phytochemicals to remove particulate matter;

separating the low and high molecular weight components using ion exchange chromatography with fractions eluted from the resin by a stepwise increase in pH;

further treating the fractions and unabsorbed material using ion exchange;

further treating the fractions and unabsorbed material by size exclusion processing using either gel permeation chromatography or ultrafiltration and/or hydrophobic chromatography; and recovering the extracted non-nutrient phytochemicals.

Pure fractions of components are recovered and concentrated by a combination of microfiltration, reverse osmosis, vacuum evaporation and freeze drying.

According to a seventh aspect of the invention, there is provided a method for extracting non-nutrient phytochemicals having GI or burn rate reducing properties from sugar cane mill mud, the method comprising the following steps:

drying the mill mud;

extracting the dried material using an aqueous or organic solvent;

repeating the extraction followed by solvent fractionation and partitioning as required; and drying the extracted material.

According to an eighth aspect of the invention, there is provided a method for lowering the GI of a food product, the method comprising combining the food product with an effective amount of a GI or burn rate lowering extract selected from the first, second, third, fourth or fifth aspects of the invention and mixtures thereof.

Preferably, the food product is a sucrose-containing product or similar. This may include an in-process product stream.

Preferably, the ratio of extract to food product is in the range from 1:10 to 1:0.5. More preferably, the ratio of extract to food product is in the range from 1:5 to 1:2.5. Most preferably, the ratio is 1:2.5.

Preferably, the GI or burn rate lowering extract further comprises nutrients. A person skilled in the art will know that the over refining of foods and therefore their metabolism can lead to a loss of nutrients, therefore it is useful for the food product to also replace those nutrients. Typically, such nutrients would comprise vitamins, minerals, proteins and other carbohydrates including complexes.

Preferably, the method further comprises combining the food product with phytochemicals not derived from sugarcane. The phytochemicals may include nutrients or non-nutrients.

Preferably, the phytochemicals are selected from the group consisting of vitamins, minerals, lipids, protein, flavonoids, polyphenols, pre-biotics, monosaccharides, disaccharides, fructo-oligosaccharides (inulins), oligosaccharides, gums, thlickeners (including but not limited to pectins, amylopectins, arabinose, starches, such as Hi-maize etc), galactose, galacto-oligosaccharides, and other carbohydrates having properties likely to improve bowel health and function, modify viscosity, further lower GI, slow burn rate or otherwise modify enzyme digestion, reduce insulinaemic response and/or change energy density.

According to a ninth aspect of the invention, there is provided a sucrose-containing product comprising:
(a) a sucrose-containing product; and
(b) an effective amount of a GI or burn rate lowering extract selected from the first, second, third or fourth aspects of the invention and mixtures thereof.

Preferably the sucrose-containing product is a highly refined product.

According to a tenth aspect of the invention, there is provided a sucrose-containing product having a GI no greater than 54.

As used herein "sucrose-containing products" include but are not limited to crystals, syrups, granules, blends and milled powders derived from sugar cane or sugar beet. It further includes any product from the sugar manufacturing process after first expressed juice or the first extract of molasses has been removed.

According to an eleventh aspect of the invention, there is provided a method for producing food products having a lower GI or burn rate, the method comprising replacing the sweetener previously used in the food product with a sucrose-containing product which has been combined with an effective amount of a GI or burn rate lowering extract selected from the first, second, third or fourth aspects of the invention and mixtures thereof.

According to a twelfth aspect of the invention, there is provided a method for improving health comprising administering an effective amount of a GI or burn rate lowering extract selected from the first, second, third, fourth or fifth aspects of the invention and mixtures thereof.

Preferably, the method further comprises combining the GI or burn rate lowering extract with a sweetener.

According to a thirteenth aspect of the invention, there is provided a method for lowering the GI of a sucrose-containing product, the method comprising combining the sucrose-containing product with bioactive compounds not derived from sugarcane having GI lowering properties according to this invention. For example such sources of these bioactive compounds may include extracts of algae, yeasts, moulds, bacteria and from other genera within the Gramineae family, and Theobroma genera. The bioactive compounds may include nutrients and non-nutrients. Preferably, the bioactive compounds are selected from the group consisting of polyphenols, flavonoids, antioxidants, pre-biotics, monosaccharides, disaccharides, fructo-oligosaccharides (inulins), oligosaccharides, galactose, galacto-oligosaccharides, vitamins, minerals, lipids, protein, gums, thickeners (including but not limited to pectins, amylopectins, arabinose, starches, Hi-maize etc), and other carbohydrates having properties likely to improve bowel health and function, lower GI, slow burn rate, reduce insulinaemic response and/or change energy density or which bind and inhibit enzymes such as amylases, glucosidases, peptidases and proteases to reduce digestion and hence glucose release into the bloodstream.

According to a fourteenth aspect of the invention, there is provided a product having a low GI comprising:
  sugar cane molasses;
  a palate-improving amount of a sweetener including, but not limited to, sucrose and fructose, and
  GI lowering carbohydrates.

Typically, the GI lowering carbohydrates are selected from the group consisting of pre-biotics, monosaccharides, disaccharides, fructo-oligosaccharides, oligosaccharides, galactose, galacto-oligosaccharides, gums, thickeners (including but not limited to pectins, amylopectins, arabinose, starches, Hi-maize etc), flavonoids and other carbohydrates having properties likely to improve bowel health and function, lower GI, slow burn rate, reduce insulinaemic response and/or change energy density or which bind and inhibit enzymes such as amylases, glucosidases, peptidases and proteases to reduce digestion and hence glucose release into the bloodstream.

According to a fifteenth aspect of the invention, there is provided a purified phytochemical extracted from sugar cane or sugar beet which has GI lowering properties. Preferably, the purified phytochemical comprises one or more of the following: lipids, phospholipids, protein, flavonoids such as anthocyanins, catechins, chalcones, flavonols and flavones, polyphenols, antioxidants, phytosterols such as 1-octacosanol, campesterol, stigmasterol, β-sitosterol, oligosaccharides such as raffinose, 1-kestose, theanderose, 6-kestose, panose, neo-kestose and nystose, and organic acids such as c-aconitic acid, citric acid, phosphoric acid, gluconic acid, malic acid, t-aconitic acid, succinic acid and lactic acid, aliphatic alcohols, vitamins, minerals, carbohydrates, gums and neutral and polar lipids.

In a preferred embodiment, there is provided a method for lowering the GI of sucrose-containing products, the method comprising combining the sucrose-containing product with a purified phytochemical extracted from sugar cane or sugar beet which has GI lowering properties.

In a further embodiment, there is provided a method for lowering the GI of food products, the method comprising combining the food product with a purified phytochemical extracted from sugar cane which has GI lowering properties.

According to a sixteenth aspect of the invention, there is provided a sweetener having a low GI comprising
  a sugar base comprising 97% to 99% of a mixture consisting of sucrose, glucose and fructose wherein preferably the combined amount of glucose and fructose is no more than 0.5% w/w of the total sweetener;
  one or more organic acids selected from the group consisting of trans-aconitic acid, oxalic, cis-aconitic, citric, phosphoric, gluconic, malic, succinic, lactic, formic and acetic acids, wherein preferably the total amount of acids in the sweetener is an amount in the range from 600 to 2100 micrograms per gram, and wherein preferably the amount of trans-acotinic acid forms the majority of the organic acids and is in an amount in the range from 200 to 600 micrograms per gram;
  one or more minerals, preferably selected from the group consisting of calcium, magnesium and potassium, wherein preferably the amount of minerals is in the range from 150 to 600 micrograms per gram, and wherein preferably the ratio of calcium to magnesium to potassium is 50:15:35;
  one or more polyphenols preferably in an amount in the range from 0.2 to 0.5 mg catechin equivalents per gram;
  one or more antioxidants wherein preferably the antioxidant activity is in the range of 0.4 to 1.2 micromoles per gram; and
  one or more polysaccharides, preferably in the range from 20 to 60 micrograms per gram.

The preferred embodiment according to this aspect of the invention provides a low GI sweetener without compromising on the taste or functionality of normal table sugar. Preferably the organic acids, minerals, polyphenols, antioxidants and polysaccharides are provided in an extract from sugar cane or sugar beets.

DETAILED DESCRIPTION OF THE INVENTION

Naturally derived refined sweeteners with added non-nutrient phytochemicals and nutrients are not known in the market. Sugar cane and sugar beet contain many non-nutrient phytochemicals including, but not limited to, aliphatic alcohols, organic acids, phospholipids, flavonoids, polyphenols and sterols. Each of the sugar processing waste streams and other in-process products such as juice or foam from the clarifying tank, molasses, mill mud, pulp and bagasse may contain a diverse range of these non-nutrient phytochemicals including soluble gums, phytosterols, waxes and phospholipids.

The present invention relates to the production of natural sugar cane and sugar beet sweeteners which have a different energy density, lower GI and slower burn rate compared to currently available highly refined sucrose products. The natural sugar cane and sugar beet sweeteners according to the invention can be produced by adding extracts of current production waste streams and in-process products or other carbohydrates to the currently available highly refined sucrose products.

Alternatively the natural sugar cane and sugar beet sweeteners according to the invention can be produced by redirecting these waste streams by changes in the current process, or by returning extracts of these waste streams back into the manufacturing process to incorporate these compounds in or on the sugarcane sweetener. The extracts from the current production waste streams add soluble gums, fibres, hydrolysed celluloses and other slowly digested carbohydrates to the sucrose product and thus lower the GI of the product and promote health. Associated health benefits include, but are not limited, to lowering the risk of diabetes and coronary heart disease.

The method for extracting the sugar cane or sugar beet nutrients and phytochemicals incorporates taking the first, second and third extracts of molasses and or sugar syrup or other molasses products, field trash, growing tips, mill mud, pulp, bagasse and in process products subjecting those extracts to fractionation, and thereafter adding these extracts back into the high purity sucrose product. Preferably, the molasses, field trash, growing tips, mill mud, bagasse and in-process products are taken from the sugar cane mill. The method may also include taking extracts of the first second and third extracts of molasses or cane or beet molasses products, then adding one or all of these fractions back into the high purity sucrose product. In one embodiment, a mix of one or more sugar phytochemicals are extracted from molasses then blended back into sucrose products.

These phytochemicals are valuable compounds and capable of promoting health when added back in higher concentration than usually found in sugar.

The method provides a means for preserving phytochemical levels occurring in the sugarcane or sugar beet feedstock in the final products. In another embodiment this is achieved by adding back one or more of the first, second and or the third cuts of molasses from the sugar refining processes. In another embodiment, phytochemicals from one or more of the cuts are extracted then added back to the sucrose product.

In another embodiment phytochemicals are extracted from sugar processing waste streams and other in-process products such as juice or foam from the clarifying tank, molasses, mill mud, and bagasse then added back into the high purity sucrose product. Various solvents can be used to extract the phytochemicals. Such food grade solvents are known in the art of phytochemical extraction including but not limited to various polar and non-polar solvents, such as alcohols. In another embodiment phytochemicals are extracted from field trash then added back to the sucrose product.

The mix of phytochemicals which is extracted from the molasses, field trash, growing tips, mill mud, pulp, bagasse and in process products is added to the sucrose products to lower GI of the finished product. In addition to having a lower GI, the natural sweetener has a slower burn rate providing sustained energy.

Sugar cane and sugar beet "non-nutrient phytochemicals" include but are not limited to flavonoids (8 subgroups: Flavonols (eg quercetin, kaempferol, myricetin andisorhanmetin); Flavones (eg luteolin, tricin and apigenin); Flavanones (eg hesperetin, naringenin anderiodictyol); Flavan-3-ols (eg catechin, gallocatechin, epicatechin, epigallocatechin, epicatechin 3-gallate, epigallocatechin 3-gallate and theaflavin); Anthocyanidins (eg cyanidin, delphinidin, malvidin, pelargonidin, peonidin and petunidin); Anthocyanosides; Curcuminoids; and Proanthocyanins) and their derivatives, including but not limited to, natural and synthetic conjugates such as glycosides, glucosides, galactosides, galacturonides, ethers, esters, arabinosides, sulphates, phosphates; aldopentoses (xylose, arabinose) aldohexoses (mannose), ketopentoses, ketohexoses (fructose), kestoses, soluble gums, aliphatic alcohols (and complexes), waxes (and complexes), polysaccharides, oligosaccharides, non-nitrogenous compounds (organic acids), minerals, mineral complexes (organic iron and other minerals), phytochemical complexes (including but not limited to glucosides, glycosides, glycosylates, esters, glucopyranosides etc), chlorophyll, phytosterols (and complexes), phytostanols (and complexes), hydrolysed celluloses and phospholipids. It is anticipated that the range or mix of non-nutrient phytochemicals can be changed during extraction by using various solvents, extraction conditions and methods. This includes but is not limited to conversion to and production of more amino sugars (glucosamine, mannosamine) and subsequent polymeric forms. Furthermore, it is also envisaged that this invention also includes synthetic derivatives, including, but not limited to, the above.

In a preferred embodiment, the extract from the molasses, field trash, growing tips, mill mud, pulp, bagasse and in process products will further comprise nutrients such as monosaccharides, aldotetroses, nitrogenous compounds (proteins, amino acids) and vitamins (biotin, choline, folic acid, niacin, pantothenic acid, riboflavin, pyridoxine, thiamine) and polyphenols (and complexes).

Without wishing to be bound by theory, certain classes of phenols, flavonoids and polyphenols or the like are reported to bind and inhibit enzymes such as amylases, glucosidases, peptidases and proteases to reduce digestion and hence glucose release into the bloodstream.

As used herein, the term "food" or "food product" includes any edible product, such as but not limited to confectioneries, supplements, snacks (sweet and savory), cocoa-containing foods, flavors, beverages, dietary supplements and formulations including supplements used in animal health and nutrition. Confectioneries refer to any sweetened foods, including but not limited to candy, chocolate, chewing gum, icings, fruit pulp based delivery systems and the like. Additional ingredients desired in the resulting food product may be added at any point in the process. Food products may also encompass for example, complex confections where chocolate is combined with and generally coats other foods such as caramels, nougat, fruit pieces, nuts, wafers, biscuits, ice cream or the like.

The natural sweeteners formed according to the invention can be used alone, in combination or added into foods to improve the functional benefits associated with such foods.

The following tables demonstrate the components in sugar beet waste products.

| Typical Analysis of Beet Pulp Pellets | | |
|---|---|---|
| Component | Dry | As Fed |
| Dry Matter | 100.00 | 91.50% |
| Moisture | 0.00 | 8.5% |
| Protein, Crude | 9.21 | 8.42% |
| TDN | 74.08 | 67.78% |
| ADF—Acid Detergent Fiber | 22.71 | 20.78% |
| NEL—Net Energy Lactation | 77.04 | 70.49 Mcal/lb |
| NEG—Net Energy Gain | 51.79 | 47.38 Mcal/lb |
| NEM—Net Energy Maintenance | 80.00 | 73.20 Mcal/lb |
| TDN—Total Digestible Nutrients | 74.08 | 67.78% |
| Fat (Ether Extract) | 0.70 | 0.64% |
| Ash | 6.22 | 5.69% |

-continued

Typical Analysis of Beet Pulp Pellets

| Component | Dry | As Fed | |
|---|---|---|---|
| Crude Fiber | 18.17 | 16.62% | |
| Calcium | 1.72 | 1.57% | |
| Phosphorus | 0.08 | 0.073% | |
| Potassium | 0.36 | 0.33% | |
| Sulfur | 0.38 | 0.35% | |
| Total Sugars | 9.56 | 8.75% | |
| Boron | 45.00 | 41.17 | ppm |
| Manganese | 86.00 | 78.70 | ppm |
| Zinc | 21.00 | 19.21 | ppm |
| Copper | 16.00 | 14.64 | ppm |
| Iron | 308.00 | 281.82 | ppm |
| Aluminum | 259.00 | 236.98 | ppm |
| Sodium | 911.00 | 833.56 | ppm |

Typical Analysis of Beet Molasses

| Component | Dry Basis | As Fed | |
|---|---|---|---|
| Dry Matter | | 78.70% | |
| Moisture | 21.30% | | |
| Protein, Crude | 11.65 | 8.51% | |
| Fiber, Crude | 0.14 | 0.11% | |
| ADF—Acid Detergent Fiber | 0.0 | 0.0% | |
| NEL—Net Energy Lactation | 0.90 | 0.71 | Mcal/lb |
| NEG—Net Energy Gain | 0.67 | 0.53 | Mcal/lb |
| NEM—Net Energy Maintenance | 1.00 | 0.78 | Mcal/lb |
| TDN—Total Digestible Nutrients | 85.65 | 67.45% | |
| Fat | 0.34 | 0.30% | |
| Ash | 10.46 | 8.40% | |
| NEF—Nitrogen Free Extract | 75.93 | 63.40% | |
| Calcium | 0.12 | 0.09% | |
| Phosphorus | 0.08 | 0.06% | |
| Potassium | 4.38 | 3.66% | |
| PH | | 7.25 | s.u. |
| Reducing Sugars | | 2.78% | |
| TSI—Total Sugars as Invert | | 54.20% | |
| Brix | | 83.40 | s.u. |

EXAMPLES

The invention will now be further explained and illustrated by reference to the following non-limiting examples.

Example 1

In this example, adding a molasses extract having GI or burn rate reducing properties according to the invention into a high purity sucrose product produced a natural sweetener. The phytochemical extract was produced using polar and non-polar solvent countercurrent extraction procedures. Other procedures known in the art including specific ion exchange or gel exclusion chromatography can also be used.

A straight "A" massecuite was boiled to a 90% purity using pure cane syrup. The massecuite footing could be either a washed high purity magma or high grade graining. Once the massecuite reached the appropriate degree of supersaturation it was fugalled to produce a sugar crystal of approximately 99.6% purity. Prior to crystals exiting the dryer, a mix of phytochemicals extracted from the first, second and third molasses extracts was sprayed onto the surface of the crystal. Resulting crystals had a higher content of natural phytochemicals. The crystals can be ground to desired particle size. The finished product is a free flowing darker crystalline mix that is dispersible in water and can be bagged and sold on the wholesale or retail markets.

Example 2

This example investigated the presence of aliphatic alcohols (policosanols) and phytosterols in fibrated sugar cane tops, bagasse and mill mud.

Extraction and Derivatisation Procedures

Fibrated cane tops were dried in a vacuum oven at 40° C. for one week. The dried material (9.58 g) was exhaustively extracted with n-heptane (boiling point 98° C.) using a soxhlet extractor for about four hours during which time at least 10 cycles were completed. The extract was dried over anhydrous sodium sulphate and evaporated to dryness to give 115 mg of oily/waxy material (1.2% yield, based on dry weight of cane tops).

Bagasse was treated in the same manner. The dried material (7.60 g) gave 50 mg of oily/waxy material (0.65% yield, based on dry weight of bagasse).

Mill mud was treated in the same manner. The dried material (9.92 g) gave 650 mg of oily/waxy material (6.53% yield, based on dry weight of mill mud).

All three extracts were saponified after melting at 80-100° C. in the presence of sodium hydroxide (5 mL, 10M solution) and heating at 95° C. for 2.5 hours. n-Heptane (5 mL, containing dihydrocholesterol as internal standard, 0.98 mg) was added to give a 2-phase system and the mixture was heated for a further two hours to ensure that the saponification was complete. In the case of the mill mud extract, a sub-sample (128 mg) was taken because of the greater quantity of this material.

The sodium hydroxide layer was removed and the organic layer washed with three lots of water. The n-heptane extract was evaporated to dryness and then extracted with boiling 95% ethanol (4×10 mL). The combined ethanol extracts were evaporated to dryness, dissolved in dry pyridine (1 mL) and N-methyl-N-trimethylsilylacetamide (2 mL) was added. The tubes containing the mixtures and a small teflon stirring bar were flushed with nitrogen and sealed. The mixtures were heated at 70° C. with stirring for one hour. A small volume (six drops of the cane tops and bagasse extracts and three drops of the mill mud extract) was transferred to glass vials (2 mL) and n-heptane (about 2 mL) was added. The mixtures were analysed by Gas Chromatography/Mass Spectrometry (GC/MS). A calibration mixture of dihydrocholesterol (1.50 mg), n-octacosanol (2.02 mg) and 3-sitosterol (1.25 mg) was treated in the same manner. Dihydrocholesterol was chosen as the internal standard because this compound could be obtained with high purity, it is more chemically stable than most sterols (which often having one or several double bonds) and it was well-separated on the HP 5-MS column from the targeted components. In addition, the major high mass fragments were different from those of the targeted components.

GC/MS Analysis

The GC/MS analyses were performed using a HP 5890N gas chromatograph (split/splitless) with a HP 5973N mass selective detector and a Gerstel MPS autosampler system. The capillary column, elution conditions and detection conditions are shown in table 1. The HP 5-MS capillary coating is polydimethylsiloxane with 5% phenyl substituents.

| Instrumental conditions for the GC/MS investigation of natural products. | |
| --- | --- |
| Gas chromatography | HP 5890 (Agilent, Palo Alto, USA) |
| GC column | HP 5-MS (length 30 m, inner diameter 0.25 mm, film thickness 0.25 um) |
| Carrier gas | He, 16.53 psi |
| Injector temperature | 260° C. |
| Oven temperature | 100° C. to 300° C. |
| Temperature program | 10° C./min |
| Mass spectrometry | HP 5973N (Agilent, Palo Alto, USA) |
| Ionization energy | 70 eV |
| Interface temperature | 260° C. |
| Scanning range | 35 amu to 555 amu |

Results and Discussion

Figure 2A:
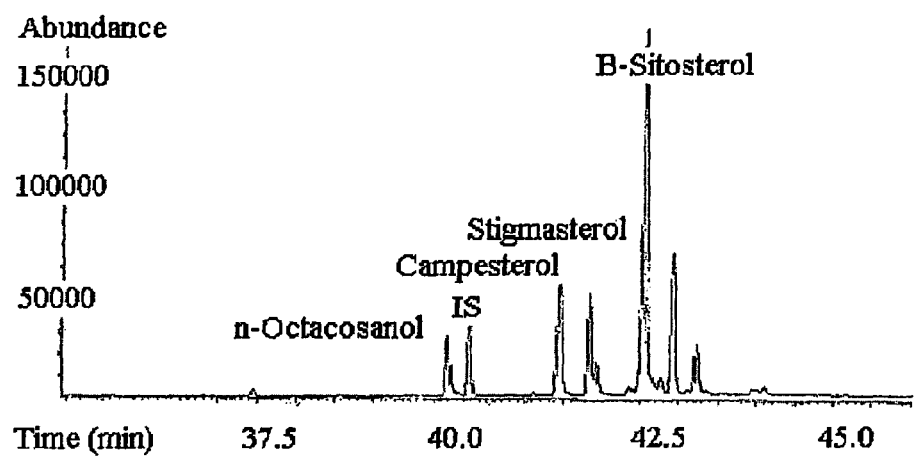
FIG. 2(a) shows a chromatogram of the extract (after derivatisation) from sugar cane bagasse.
Figure 2B:
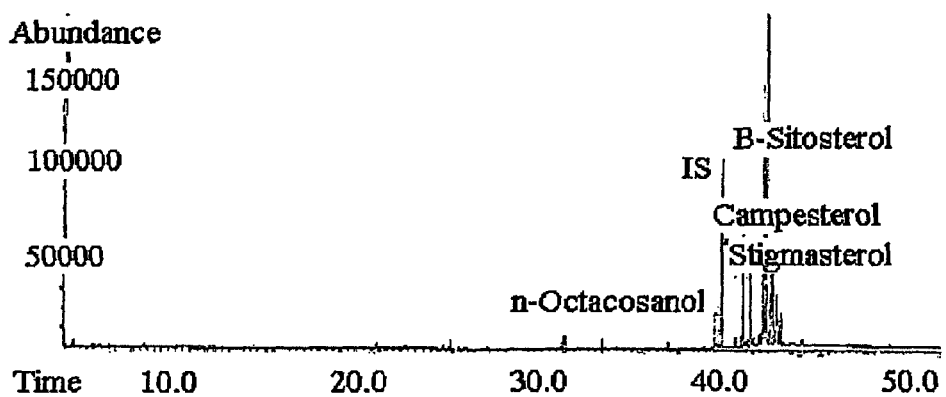
FIG. 2(b) shows an expanded section of the chromatogram of the extract (after derivatisation) from sugar cane bagasse.
Figure 3A:
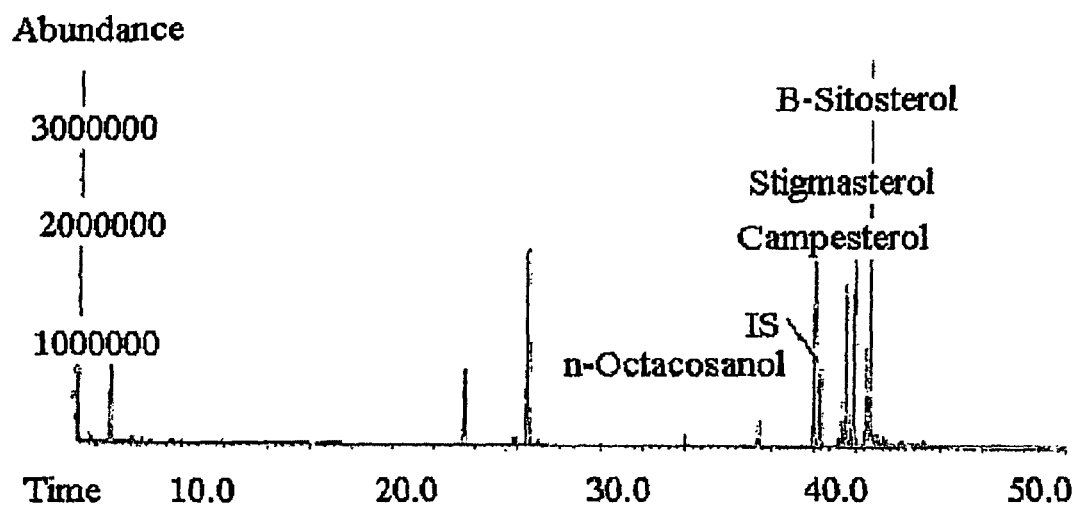
FIG. 3(a) shows a chromatogram of the extract (after derivatisation) from sugar cane mill mud.
Figure 3B:
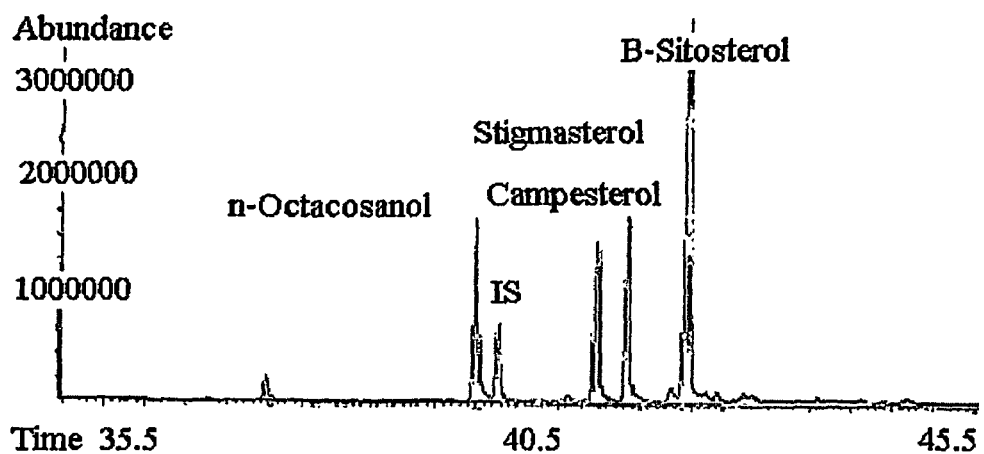
FIG. 3(b) shows an expanded section of the chromatogram of the extract (after derivatisation) from sugar cane mill mud.

The chromatograms of the three extracts after derivatisation are shown in FIGS. 1-3.

(Note: the components shown in the chromatogram are primarily trimethylsilyl derivatives.)

The removal of the sodium hydroxide solution following saponification resulted in the removal of acidic components and more water-soluble compounds from the materials that subsequently were analysed. These compounds included phenolic compounds known to be present in cane products. Other approaches are needed to analyse for these components. The extraction of materials with ethanol provided a separation of the non-polar components such as alkanes from the more polar components that included the alcohols and sterols (the materials in the extracts analysed), although these compounds are only marginally more polar.

The yield of individual components on the basis of dry weight of cane material or mill mud was recorded rather than on the basis of weight of extractive because the conditions of extraction and processing of the crude waxes in an industrial process will affect the yield of each component.

The compounds were converted to their trimethylsilyl derivatives so that they could be analysed by GC/MS. All determinations were based on peak area of components. The determination of campesterol and stigmasterol was based on the assumption that their response factors were similar to 3-sitosterol. This seems reasonable because of the overall similarity of the mass spectra of all three sterols, and it is the abundance of ions and pattern that determine the peak areas of the different components.

The relative proportions of alcohols were determined from their peak areas but when occurring as very small peaks (as most were), there is the greater likelihood of other co-eluting components leading to an overestimation of their concentration. A more accurate estimation can be made on the basis of the peak areas of the base peak in the mass spectrum, i.e. the [M−15]+ ion fragment, where M is the molecular weight.

The content of n-octacosanol and the three major sterols in the cane tops, bagasse and mill mud are shown in Tables 1-3.

TABLE 1

| Content of n-octacosanol and sterols in cane tops | | |
| --- | --- | --- |
| Retention time (min) | Compound | Content (mg/kg of dried material) |
| 39.98 | n-octacosanol | 198 |
| 41.45 | Campesterol | 210 |
| 41.84 | Stigmasterol | 140 |
| 42.54 | β-Sitosterol | 590 |
| | Total (3 sterols) | 940 |

TABLE 2

| Content of n-octacosanol and sterols in bagasse | | |
| --- | --- | --- |
| Retention time (min) | Compound | Content (mg/kg of dried material) |
| 39.98 | n-octacosanol | 67 |
| 41.45 | Campesterol | 100 |
| 41.84 | Stigmasterol | 65 |
| 42.54 | β-Sitosterol | 300 |
| | Total (3 sterols) | 463 |

TABLE 3

| Content of n-octacosanol and sterols in mill mud | | |
| --- | --- | --- |
| Retention time (min) | Compound | Content (g/kg of dried material) |
| 39.99 | n-octacosanol | 2.61 |
| 41.45 | Campesterol | 1.30 |
| 41.84 | Stigmasterol | 1.34 |
| 42.54 | β-Sitosterol | 2.89 |
| | Total (3 sterols) | 5.52 |

The cane tops gave a higher yield (about 2-fold) of these compounds compared with bagasse but the mill mud provided the richest yield. Small quantities of compounds having mass spectra indicative of sterols were detected in the mill mud extract. These components with retention times of 42.78, 42.92 and 43.23 minutes amounted to only about 3% (each) of the β-sitosterol content and no attempt was made to identify them. Whilst n-octacosanol was the major component in the group of alcohols present, small quantities of even carbon chain homologues were also detected (see earlier) along with the closely related odd carbon chain homologues—see tables. The content of alcohols in the cane tops, bagasse and mill mud are shown in Tables 4-6.

TABLE 4

| Alcohols in cane tops | | | |
| --- | --- | --- | --- |
| Retention time (min) | Compound | Number of carbon atoms | Content (mg/kg of dry material) |
| 21.85 | n-Tetradecanol | 14 | 4 |
| 23.47 | n-Hexadecanol | 16 | 8 |
| 25.47 | n-Octadecanol | 18 | 18 |
| 28.80 | n-Eicosanol | 20 | 7 |
| 31.89 | n-Docosanol | 22 | 2 |
| 34.77 | n-Tetracosanol | 24 | n.d.* |
| 37.45 | n-Hexacosanol | 26 | 18 |
| 38.66 | n-Heptacosanol | 27 | 2 |
| 40.27 | n-Octacosanol | 28 | 198 |
| 41.12 | n-Nonacosanol | 29 | 15 |
| 42.36 | n-Triacontanol | 30 | 38 |
| 45.18 | n-Dotriacontanol | 32 | n.d. |

*n.d. less than 1 mg/kg of dry material

TABLE 5

| Alcohols in bagasse | | | |
| --- | --- | --- | --- |
| Retention time (min) | Compound | Number of carbon atoms | Content (mg/kg of dry material) |
| 21.85 | n-Tetradecanol | 14 | 2 |
| 23.47 | n-Hexadecanol | 16 | 1 |

TABLE 5-continued

Alcohols in bagasse

| Retention time (min) | Compound | Number of carbon atoms | Content (mg/kg of dry material) |
|---|---|---|---|
| 25.47 | n-Octadecanol | 18 | 1 |
| 28.80 | n-Eicosanol | 20 | n.d.* |
| 31.89 | n-Docosanol | 22 | 4 |
| 34.77 | n-Tetracosanol | 24 | 1 |
| 37.45 | n-Hexacosanol | 26 | 3 |
| 38.72 | n-Heptacosanol | 27 | n.d. |
| 40.28 | n-Octacosanol | 28 | 67 |
| 41.12 | n-Nonacosanol | 29 | 5 |
| 42.37 | n-Triacontanol | 30 | 7 |
| 45.18 | n-Dotriacontanol | 32 | n.d. |

*n.d. less than 1 mg/kg

TABLE 6

Alcohols in mill mud

| Retention time | Compound | Number of carbon atoms | Content (g/kg of dry material) |
|---|---|---|---|
| 21.83 | n-Tetradecanol | 14 | 0.01 |
| 23.47 | n-Hexadecanol | 16 | 0.84 |
| 25.47 | n-Octadecanol | 18 | n.d.* |
| 28.80 | n-Eicosanol | 20 | n.d. |
| 31.88 | n-Docosanol | 22 | 0.01 |
| 34.77 | n-Tetracosanol | 24 | 0.02 |
| 37.46 | n-Hexacosanol | 26 | 0.37 |
| 38.73 | n-Heptacosanol | 27 | 0.03 |
| 39.99 | n-Octacosanol | 28 | 2.61 |
| 41.12 | n-Nonacosanol | 29 | 0.28 |
| 42.36 | n-Triacontanol | 30 | 0.28 |
| 45.18 | n-Dotriacontanol | 32 | 0.19 |

*n.d. less than 0.01 g/kg

Discussion

The major components present in the extracts of all three sugar cane derived materials were long-chain alcohols and sterols. The major alcohol was n-octacosanol, which occurred with smaller quantities of other closely-related alcohols with those having an even number of carbon atoms dominating. The major sterols were campesterol, stigmasterol and β-sitosterol but minor quantities of other sterols also were present, based on mass spectral data.

Example 3

Method for Molasses Fractionation

The following flowchart illustrates the process used to extract the GI lowering phytochemicals from sugar cane molasses.

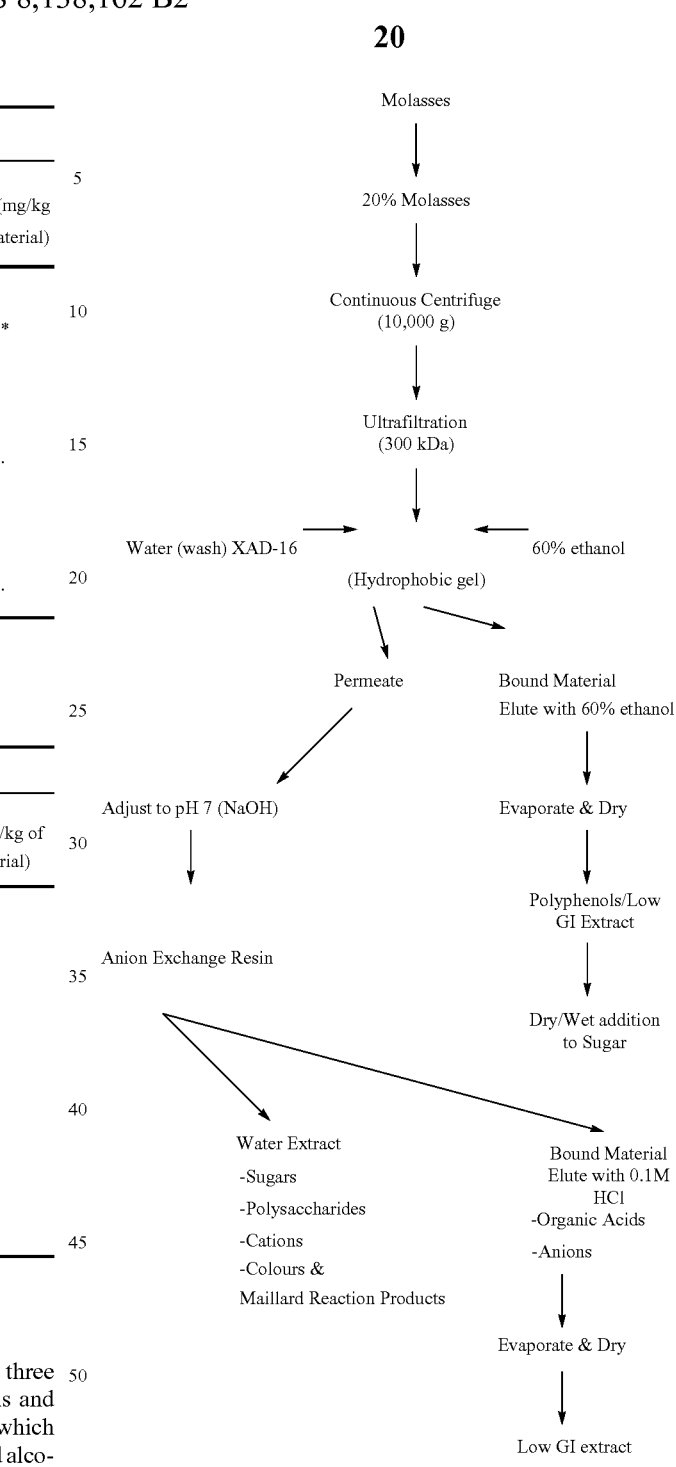

The following analysis was completed.

Figure 5:
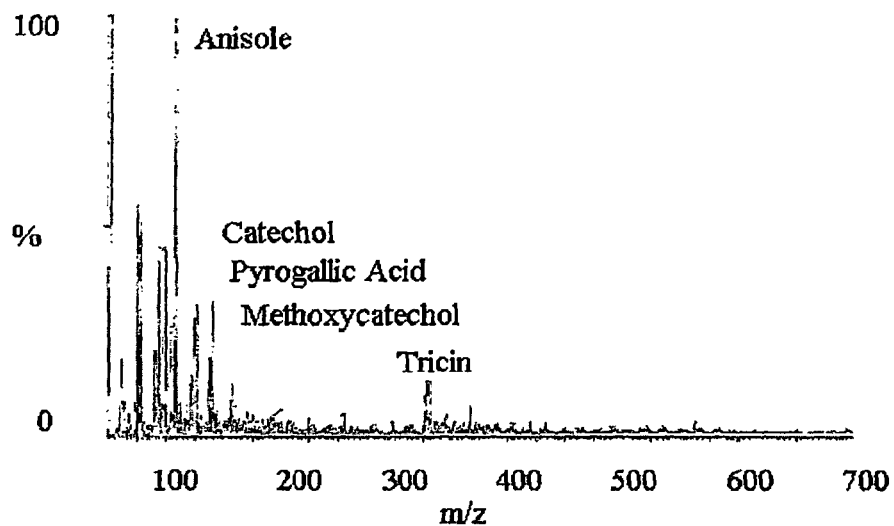
FIG. 5 is the ESMS trace for the bound extracted components from Example 3.
Figure 6:
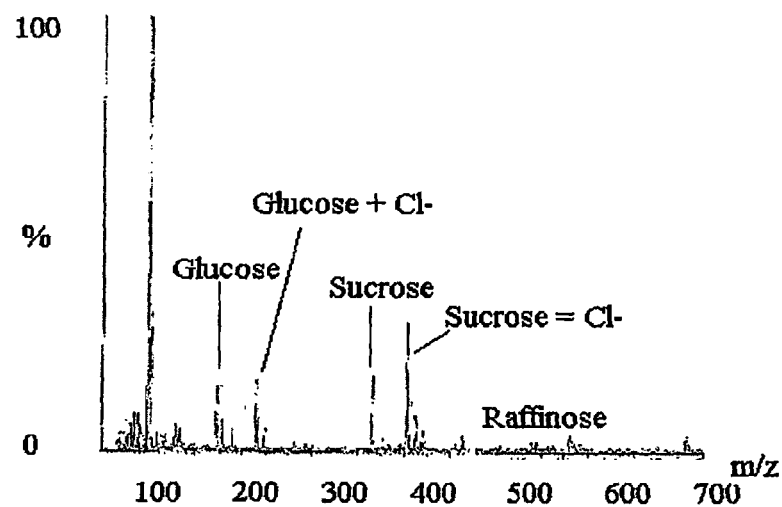
FIG. 6 is the ESMS trace for the unbound extracted components from Example 3.
Figure 7:
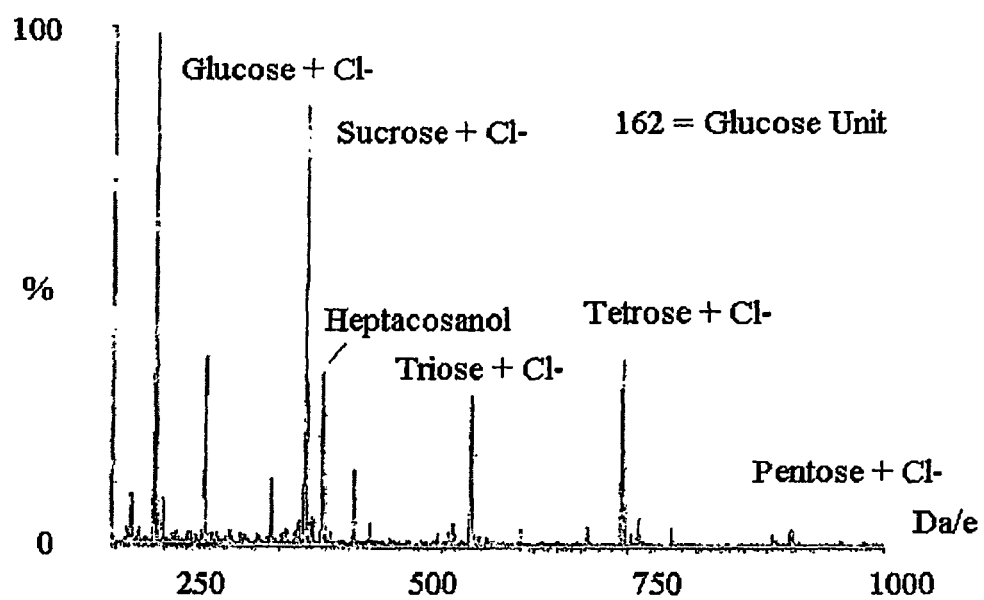
FIG. 7 is the ESMS trace for the crude sugar cane molasses starting material used in Example 3.

Electrospray Mass Spectrometry (ES/MS) was conducted on a Micromass Platform ES/MS. The samples were dissolved in Methanol/Water (80:20) and injected into a 20 μl loop and eluted with methanol/water (80:20) at 20 μl/min. MS analysis was conducted in negative ion mode with a cone voltage of 40 kV and a mass range of 50-700 Da. FIGS. 5 to 7 show the resultant traces.

Figure 8:
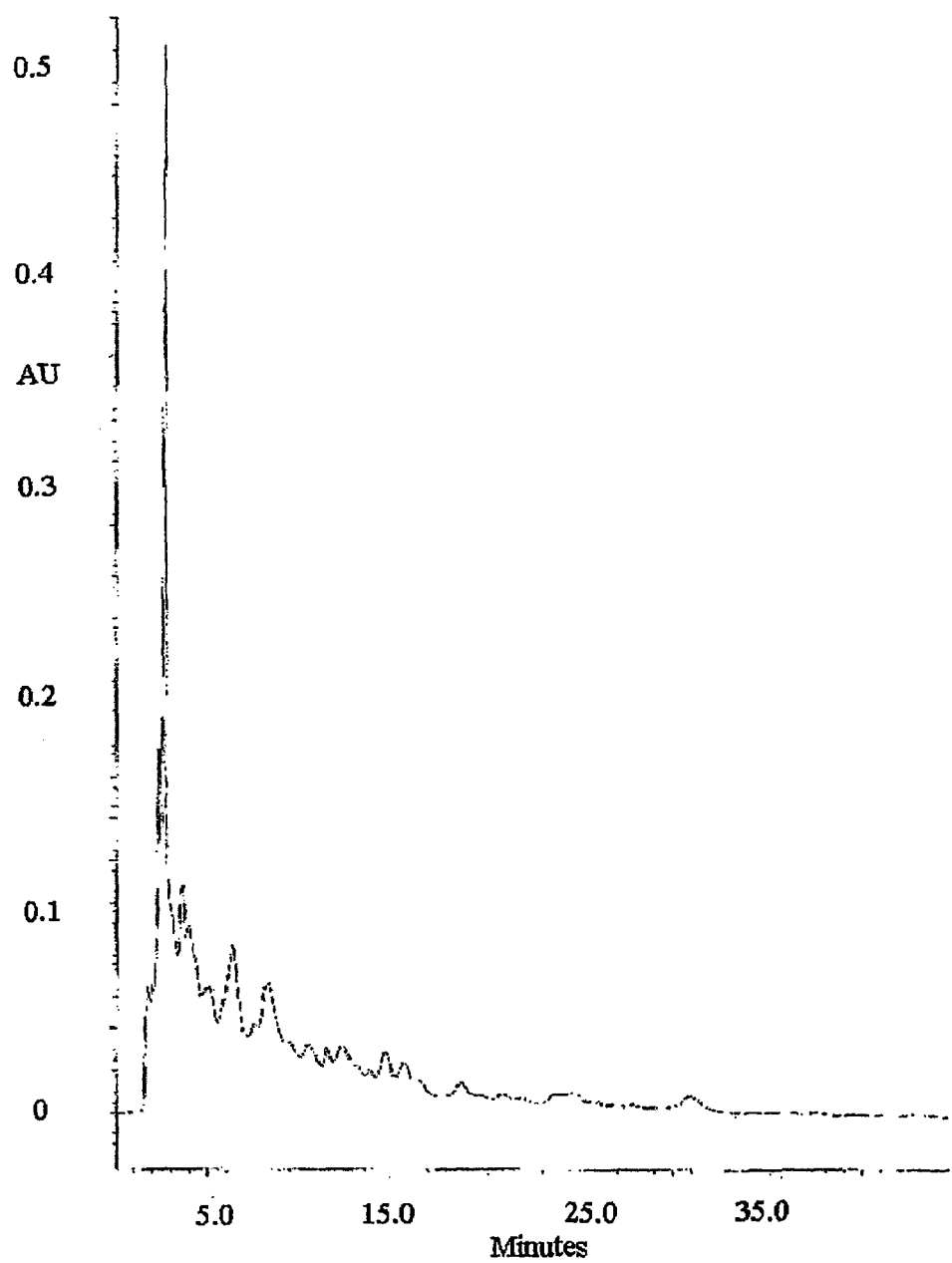
FIG. 8 is the HPLC trace for the extracted material from Example 3.
Figure 9:
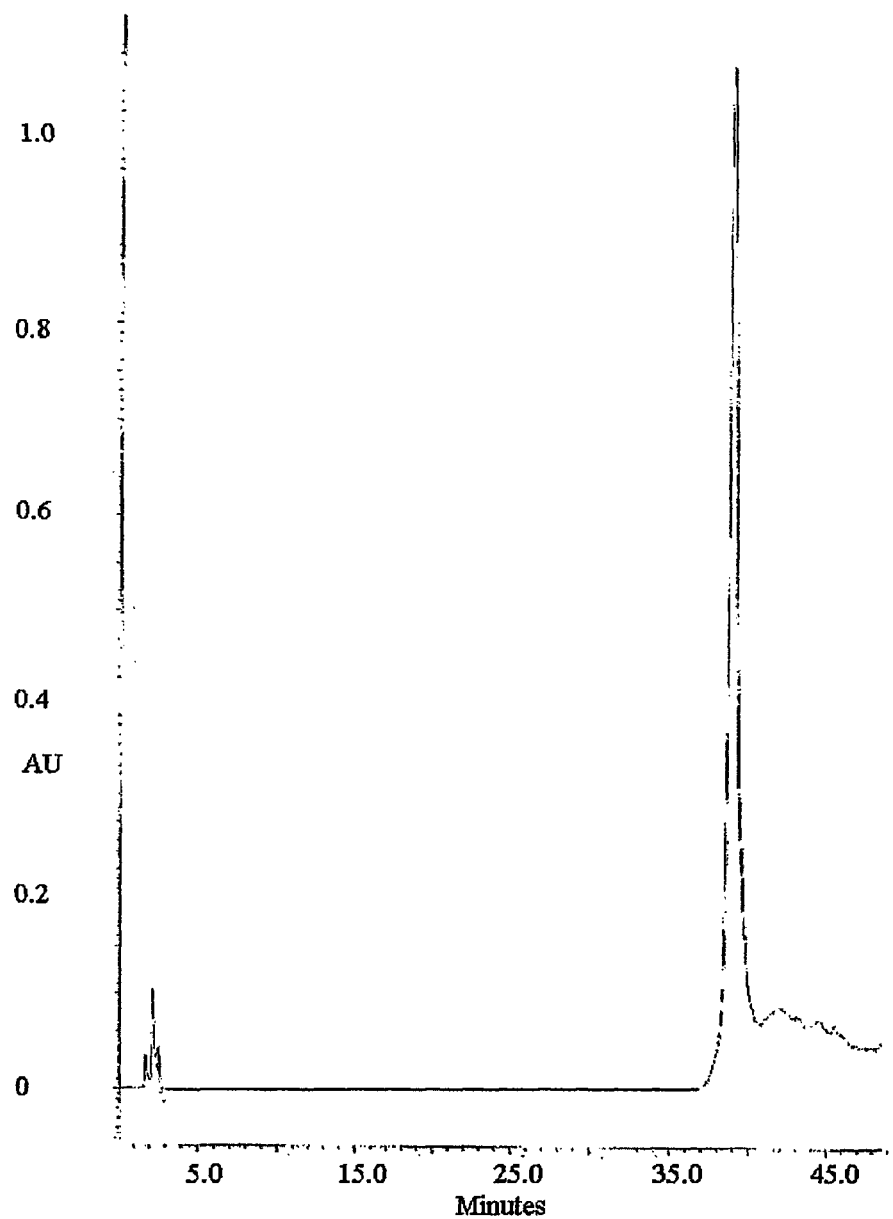
FIG. 9 is the HPLC trace for the crude sugar cane molasses starting material used in Example 3.

High Pressure Liquid Chromatography (HPLC) was conducted using a Waters 600 with auto-injector. The column was a Keystone Scientific ODS-Hypersil (150×4.6 mm). The sample was dissolved in 50% acetonitrile/water and 10 μl was injected. The sample was eluted with acetonitrile/20 mmol acetic acid (15:85) at 1 ml/min. The sample was detected at 210-400 nm with an extracted wavelength of 220 nm. FIGS. 8 and 9 show the resultant traces.

Discussion

The traces show that the low GI extract (bound material) consisted mostly of low molecular weight polyphenols with the sucrose, fructose and glucose removed.

Example 4

This example investigated the content of lipids and proteins in sugar cane waste streams to assist with understanding the GI lowering properties of extracts from molasses, bagasse, mill mud and field trash/fibrated cane tops.

Methods

Lipid content from bagasse was determined by the method of Folch et al (1957). Phospholipid level was determined by the method of Ames and Dubin (1960). Organic phosphorus was multiplied by 25 to give the phospholipid content. Total solids content was determined using the Australian Standard Method AS2300.1.1. Total nitrogen levels were determined using the AOAC method AOAC (2000) 920.176. Total nitrogen was multiplied by 6.25 to give the protein content. Polyphenol content was determined by a procedure based on that of Kim et al (2003) and used catechin as the standard. HPLC: The phospholipid profile of the lipid extract was obtained by normal phase HPLC using a Platinum silica column with a gradient elution system of trimethylpentane, iso-propanol/chloroform, and iso-propanol/water. Six peaks were obtained, of which three were identified as phospholipids: phosphatidyl serine; phosphatidyl ethanolamine; and lysophosphatidyl ethanolamine (see FIG. 4). These peaks accounted for approximately 15% of the total peak area. The remaining peaks were unidentified polar lipids, possibly glycolipids, but this has not been confirmed. Neutral lipids were also present, eluting immediately after the solvent peak (see FIG. 4).

Quantification of the phospholipid peaks indicated that 0.077 mg II/mg lipid were present. This is lower than the value obtained by the procedure of Ames and Dubin (above), 0.095 mg PL/mg lipid. It is possible that other phospholipid components were masked by the large unidentified peaks. Previous studies have shown good agreement between these two procedures.

Results

TABLE 7

| Sample | Lipid (%, m/m, wet wt) | Phospholipid (%, m/m, wet wt) | Total solids (%, m/m, wet wt) | Protein (TN × 6.25) (%, m/m, wet wt) |
|---|---|---|---|---|
| Bagasse | 0.43 | 0.001 | 51.46 | 0.70 |
| Clarifying tank | 0.10 | 0.012 | 16.82 | 0.29 |
| Mill mud | 0.44 | 0.061 | 26.19 | 0.09 (TN) |
| Molasses | 0.26 | 0.011 | 82.25 | 2.76 |

TABLE 8

Total Protein in Cane Samples

| Sample | Protein (N × 6.25) (g/100 g) |
|---|---|
| First Expressed Juice | 0.3 |
| Final Juice | <0.1 |
| Syrup extracted from the clarified juice | 0.5 |
| Low pol Molasses | 2.8 |
| Mill Mud | 2.0 |
| Cane Tops Extract | 0.9 |

Discussion

Figure 4:
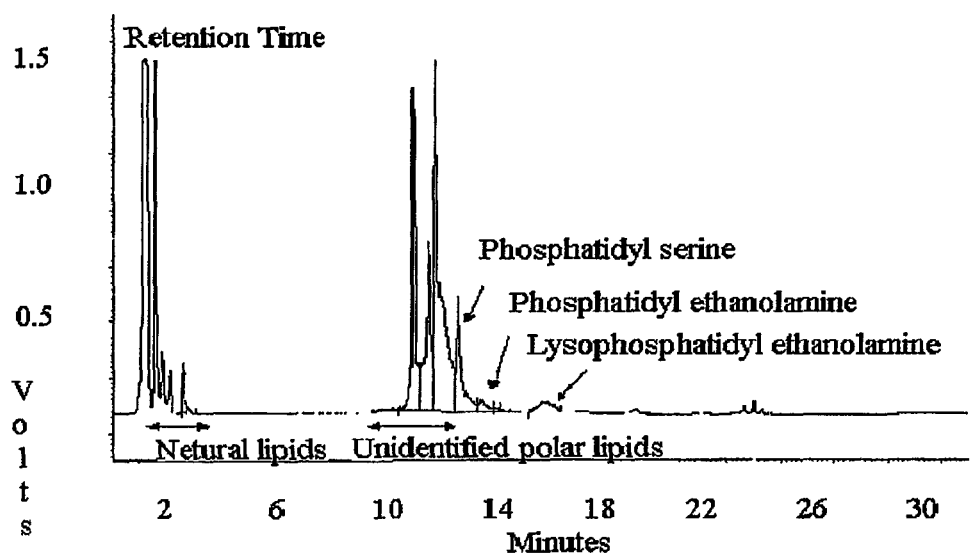
FIG. 4 shows a polar lipid profile extracted from sugar cane.

Analysis of juice and foam from the clarifying tank detected surfactants phosphatidyl serine, phosphatidyl ethanolamine and lysophosphatidyl ethanolamine. Although the foam sample had a low lipid content, a broad range of neutral and unidentified polar lipids were detected (FIG. 4). In further analysis lipid, phospholipid and protein were detected in a variety of samples. Lipid was most concentrated in mill mud and bagasse.

Bagasse was also a concentrated source of protein. With extraction systems known in the art this fraction could be recovered. The most concentrated source of protein was surprisingly found in low pol-molasses.

Example 5

This example investigated the antioxidant content of sugar cane waste streams to assist with understanding the GI lowering properties of extracts from molasses, bagasse, mill mud and field trash/fibrated cane tops.

A catechin equivalent assessment of First Expressed juice, final juice, syrup, molasses, low pol sugar, mill mud, cane tops and foam were undertaken.

Results

TABLE 9

| | Total Antioxidant Potential (*CE = catechin equivalents) | |
|---|---|---|
| Sample | (mg CE*/mL) | (mg CE*/g dry matter) |
| First Expressed Juice | 0.75 | 3.40 |
| Final Juice | 0.12 | 8.76 |
| Syrup extracted from the clarified juice | 2.89 | 3.43 |
| Molasses | 23.58 | 30.00 |
| Low pol Sugar | — | 2.34 |
| Filtrate | 0.44 | 3.64 |
| Cane tops | 0.44 | 13.54 |
| Foam | 0.23 | 3.75 |
| Mill Mud | — | 3.17 |
| High Pol Sugar | 0.44 | — |

TABLE 10

Antioxidant potential of sugar cane extracts vs other polyphenol sources

| Sample | Polyphenols (mg catechin equivs/g) | Anti-oxidants (µmoles/g) |
|---|---|---|
| Dark Chocolate | 23.9 | NT |
| Milk Chocolate | 7.25 | 18.3 |
| Cocoa liquor | 41.8 | 110 |
| Grape Seed Powder | 301.5 | 1146 |
| Grape Skin Extract | 54.5 | 181 |
| Mixed Berry Snack | 12.3 | 9.33 |
| Mixed Juice | 3.35 | NT |
| Mill mud | 14.7 | 26.8 |
| Molasses | 17.87 | 32.58 |
| High Pol sugar | 0.25 | 0.44 |

Discussion

The analysis revealed that molasses was a surprisingly concentrated source of antioxidants and similar to dark chocolate. In a purified form, it is likely that molasses antioxidants will be at least as effective as antioxidants from other sources such as grape seed powder.

These compounds are important to human health and can be utilized for their health promoting potential.

These compounds can be extracted then added back into sugarcane products to lower GI and promote health.

Example 6

This example investigated the oligosaccharide, polysaccharide and other gum content of sugar cane waste streams to assist with understanding the GI lowering properties of extracts from molasses, bagasse, mill mud and field trash/fibrated cane tops.

Results

TABLE 11

Total polysaccharide content of sugarcane processing and waste streams

| Sample | Total polysaccharide (mg/kg) |
|---|---|
| FE Juice | 7832 |
| Final Juice | 38561 |
| Syrup | 5258 |
| Low pol molasses | 26610 |
| Low pol sugar | 3797 |
| Cane Tops Extract | 17063 |

Discussion

Final juice and low pol molasses were respectively the most concentrated polysaccharide sources. On a dry weight basis low pol-molasses is however, the most concentrated. A crude extract of cane tops, molasses and final juice is used in sugarcane products to lower GI and improve health potential.

Example 7

This example investigated the acid content of sugar cane waste streams to assist with understanding the GI lowering properties of extracts from molasses, bagasse, mill mud and field trash/fibrated cane tops.

TABLE 12

Organic acid analysis by ICP-MS

| Samples | Organic acid (ppm on dry solids) | | | | | | | | | | |
|---|---|---|---|---|---|---|---|---|---|---|---|
| | Oxalic | c-aconitic | citric | phosphoric | Gluconic | malic | t-aconitic | succinic | lactic | formic | acetic |
| First Expressed Juice | 221 | 662 | 1091 | 2979 | 1310 | 1311 | 6157 | 132 | 36 | 23 | 485 |
| Final Juice | 778 | 1199 | 1258 | 4521 | 11678 | 1650 | 2811 | 395 | 0 | 0 | 4406 |
| Syrup | 217 | 320 | 1067 | 893 | 1568 | 1482 | 6616 | 324 | 994 | 113 | 4723 |
| Low pol Molasses | 355 | 1177 | 749 | 726 | 1713 | 1057 | 10345 | 200 | 309 | 119 | 1006 |
| Low pol sugar | 206 | 731 | 676 | 504 | 1203 | 786 | 3193 | 243 | 1348 | 203 | 3714 |
| Cane Tops extract (soluble solids) | 598 | 3043 | 2133 | 9235 | 7025 | 6938 | 49075 | 625 | 0 | 0 | 0 |
| Cane tops extract (total solids) | 81 | 413 | 290 | 1254 | 954 | 942 | 6665 | 85 | 0 | 0 | 0 |

Discussion

First Expressed juice, final juice, syrup, low pol molasses, low pol sugar, and cane tops were assayed for organic acid content. Surprisingly, large quantities of many organic acids were detected across most of the samples analyzed. Cane tops and low pol molasses were the most concentrated sources and lower GI or improve health potential when conserved during processing or extracted then added back to sugar products.

Example 8

This example investigated the nutrient (cations, anions, vitamins and minerals) content of sugar cane waste streams to assist with understanding the GI lowering properties of extracts from molasses, mill mud and field trash/fibrated cane tops.

Results

TABLE 13

Anion analysis by chromatography

Anions (ppm on dry solids)

| Sample | Fluoride | Chloride | Nitrite | Bromide | Nitrate | Phosphate | Sulphate |
|---|---|---|---|---|---|---|---|
| First Expressed Juice | 186 | 3084 | 75 | 24 | 0 | 1277 | 2175 |
| Final Juice | 122 | 1738 | 0 | 118 | 74 | 1637 | 1734 |
| Syrup | 133 | 3033 | 0 | 0 | 0 | 125 | 1834 |
| Low pol Molasses | 885 | 22262 | 283 | 552 | 9 | 717 | 13279 |
| Low pol sugar | 187 | 2402 | 0 | 78 | 22 | 141 | 1173 |
| Mill Mud | 18 | 495 | 0 | 32 | 42 | 509 | 419 |
| Cane Tops Extract | 179 | 2668 | 0 | 5 | 2 | 680 | 3091 |
| Bagasse | 10 | 153 | 2 | 0 | 3 | 160 | 196 |

TABLE 14

Cations identified by ICP-MS

Element (ppm)

| | Ca | | Fe | | K | | Mg | | Mn | | Na | | Zn | |
|---|---|---|---|---|---|---|---|---|---|---|---|---|---|---|
| Sample | Conc | S.D. | Conc. | S.D. | Conc. | S.D. | Conc | S.D. | Conc | S.D. | Conc | S.D. | Conc | S.D. |
| First Expressed Juice | 132 | 2 | 175 | 2 | 1260 | 12 | 164 | 1 | 15.9 | 0.1 | 14.1 | 0.1 | 2.40 | 0.06 |
| Final Juice | <=0.05 | | 15.2 | 0.2 | 15.0 | 21.4 | 7.59 | 0.15 | 1.06 | 0.03 | 0.227 | 0.003 | <=0.05 | |
| Syrup | 1280 | 19 | 12.7 | 0.7 | 4840 | 16 | 567 | 3 | 7.56 | 0.03 | 125 | 1 | 0.891 | 0.025 |
| Low pol Molasses | 8444 | 13 | 120 | 2 | 25800 | 55 | 3860 | 10 | 54.4 | 0.4 | 2090 | 15 | 3.60 | 0.19 |
| Low pol sugar | 1120 | 12 | 12.3 | 0.1 | 3260 | 39 | 462 | 2 | 5.99 | 0.20 | 236 | 4 | <=0.05 | |
| Cane Tops Extract | 507 | 5 | 135 | 1 | 3970 | 34 | 418 | 3 | 20.0 | 0.1 | 6.08 | 0.15 | 11.0 | 0.1 |
| Bagasse | 290 | 8 | 162 | 2 | 224 | 11 | 176 | 1 | 14.9 | 0.2 | 19.0 | 0.1 | <=0.05 | |

TABLE 15

Vitamins

| Sample | Ascorbic Acid (mg/100 g) | Beta-Carotene (ug/100 g) |
|---|---|---|
| First Expressed Juice | <1 | Not tested |
| Final Juice | <1 | 6.6 |
| Low pol Molasses | <1 | Not tested |
| Low pol sugar | <1 | Not tested |
| Mill Mud | Not tested | 580 |
| Cane Tops Extract | <1 | 62 |

TABLE 16

Vitamins

| Sample | Niacin (Vitamin B3) (mg/100 g) | Pantothenic Acid (Vitamin B5) (mg/100 g) | Total folates (ug/100 g) | Vitamin K1 (ug/100 g) |
|---|---|---|---|---|
| First Expressed Juice | <0.5 | <1 | <30 | Not tested |
| Final Juice | <0.5 | <1 | <30 | <10 |
| Low pol Molasses | 3.8 | 1.5 | 10 | Not tested |
| Low pol sugar | 0.5 | 1 | <30 | Not tested |
| Mill Mud | Not tested | Not tested | Not tested | <10 |
| Cane Tops Extract | >0.5 | 1 | 20 | <10 |

TABLE 17

Mineral content by ICP-MS elemental analysis

| Sample | Results (Units - mg/Kg) | | | | | | | |
|---|---|---|---|---|---|---|---|---|
| | Ca | Fe | K | Mg | Mn | Na | Pb | Zn |
| Molasses C | 5700 | 68.30 | 27400.0 | 3000 | 41.10 | 468 | 0.06 | 5.82 |
| Molasses D | 5960 | 72.80 | 20700.0 | 2520 | 44.30 | 552 | 0.05 | 4.50 |
| Low pol sugar C | 1130 | 9.46 | 4910.0 | 590 | 10.80 | 50 | 0.02 | 1.65 |
| Low pol sugar D | 1290 | 15.50 | 4400.0 | 547 | 12.30 | 78 | 0.03 | 1.39 |
| Foam C | 83 | 24.80 | 309.0 | 77 | 7.06 | 6 | 0.03 | 1.27 |
| Foam D | 107 | 68.30 | 313 | 63.00 | 7 | 11.30 | 0.11 | 1.69 |
| Mixed Juice C | 192 | 45.50 | 845.0 | 224 | 17.10 | 6 | 0.05 | 1.36 |
| Mixed Juice D | 160 | 86.80 | 611.0 | 107 | 13.80 | 16 | 0.07 | 1.07 |
| Raw sugar | 94 | 0.51 | 67.5 | 28 | 0.65 | <=.05 | <=.005 | 0.01 |

Example 9

In this example, sugar products containing GI lowering substances according to the invention were prepared.

A high pol sugar base was prepared containing 98.88% sucrose (24.72 g), 0.07% glucose (0.0175 g) and 0.07% fructose (0.0175 g). The term "pol" refers to the level of sucrose in sugar products. High pol describes products with at least 98.5% sucrose. Any product with less than 98.5% sucrose is referred to as "low pol".

A low pol sugar base was prepared containing 88.5% sucrose (22.125 g), 1.42% glucose (0.355 g) and 1.55% fructose (0.3875 g).

Formulation A: high pol sugar base was combined with 20% added molasses extract as prepared in Example 3 above. Formulation A has 79.104% sucrose (19.776 g), 0.056% glucose (0.014 g) and 0.056% fructose (0.014 g).

Formulation B: high pol sugar base was combined with 20% galactose (5 g). Formulation B has 79.104% sucrose (19.776 g), 0.056% glucose (0.014 g) and 0.056% fructose (0.014 g).

Formulation C: low pol sugar base was combined with 20% galactose (5 g). Formulation C has 70.8% sucrose (17.7 g), 1.136% glucose (0.284 g) and 1.24% fructose (0.31 g)

Example 10

In this example, the effect of the addition of organic acids to the pH and taste of high pol sugar was investigated.

Procedure

Molasses organic acid extract: A mixture of organic acids extracted from molasses was prepared and had the following composition (18.2 mg of organic acids can be extracted from 1 gram of molasses solids):

| Organic acid | Amount(g) |
|---|---|
| cis-aconitic | 2 |
| citric | 1 |
| phosphoric | 0.7 |
| gluconic | 0.5 |
| malic | 1.5 |
| trans-aconitic | 12 |
| succinic | 0.3 |
| lactic | 0.2 |

This solution was added to 50 g of the high pol sugar base from Example 9 at four levels of addition, equivalent to 1%, 2%, 5% and 10% molasses acids in sugar (m/v).

The mixtures were dissolved in water to a final volume of 500 mL.

The control contained the high pol sugar base with no added molasses acids.

Results

The pH of each formulation was tested.

| Amount of added organic acid (% m/v) | pH |
|---|---|
| 0 | 6.62 |
| 1 | 5.45 |
| 2 | 4.87 |
| 5 | 4.08 |
| 10 | 3.66 |
| Molasses organic acid extract | 1.68 |

Figure 10:
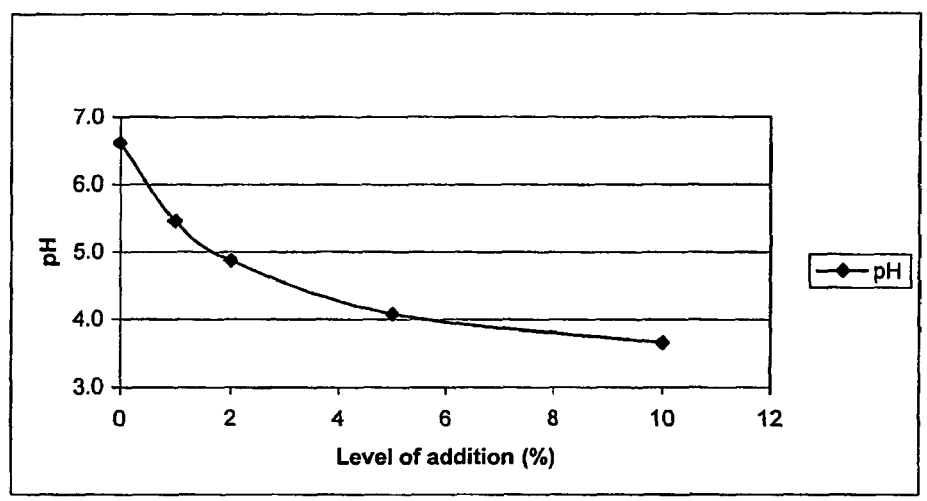
FIG. 10 is a plot of the pH for the different formulations in Example 10.

The results are plotted in FIG. 10.

The taste was tested by 5 tasters. The testers reported that all of the samples tasted sweet. There was very little difference in taste between the control and the formulations containing 1%, 2% and 5% of the molasses organic acid extract. However, the formulation with 10% of the molasses organic acid extract was slightly less sweet and had a different taste with a slightly sour/bitter aftertaste.

Conclusion

Up to 5% of molasses organic acid extract can be added to high pol sugar base without interfering with the taste of the sweetener.

Example 11

This example investigates the glycaemic index of sweeteners prepared according to the invention.

Formulations Tested

Six (6) treatments were prepared for GI testing at the Human Nutrition Unit, University of Sydney.

The High Pol Sucrose used in the treatments comprised 99% total sucrose, glucose and fructose (wherein the amount of glucose and fructose was no more than 0.5%) and 1% of a mixture of organic acids, minerals, polyphenols, antioxidants and polysaccharaides. This mixture consisted of the following:

600 to 2100 micrograms per gram of a mixture of trans-aconitic acid, oxalic, cis-aconitic, citric, phosphoric, gluconic, malic, succinic, lactic, formic and acetic acids, wherein most of the mixture consisted of trans-acotinic acid in an amount in the range from 200 to 600 micrograms per gram;

150 to 600 micrograms per gram of minerals with the ratio of calcium to magnesium to potassium being 50:15:35;

0.2 to 0.5 mg catechin equivalents per gram of polyphenols;

antioxidants so that the antioxidant activity is in the range of 0.4 to 1.2 micromoles per gram; and 20 to 60 micrograms per gram of polysaccharides.

1 High Pol Sucrose alone
2 Low Pol Sucrose alone (contains more free glucose than High Pol Sucrose)
3 High Pol Sucrose plus galactose in a 4:1 ratio
4 Low Pol Sucrose plus galactose in a 4:1 ratio
5 High Pol Sucrose plus molasses extract from Example 3 in a 5:1 ratio
6 High Pol Sucrose plus molasses extract from Example 3 in a 2.5:1 ratio Treatments 1 to 4 contained base sugar±galactose to give a 50 g carbohydrate load (500 mL test solution). Sixteen (16) samples were prepared per treatment: fifteen (15) for GI testing; and one (1) retained by QDPI&F.

| Treatment | Base | Base (Average weight) | Standard deviation | Galactose (average weight) | Standard deviation |
|---|---|---|---|---|---|
| 1 | High Pol Sucrose | 50.495 | 0.001 | — | — |
| 2 | Low Pol Sucrose | 54.666 | 0.002 | — | — |
| 3 | High Pol Sucrose | 40.236 | 0.001 | 10.160 | 0.003 |
| 4 | Low Pol Sucrose | 43.482 | 0.006 | 10.151 | 0.004 |

The carbohydrate loads in these treatments are shown below.

| Treatment | Carbohydrate load (average) | Standard deviation |
|---|---|---|
| 1 | 50.000 | 0.001 |
| 2 | 50.003 | 0.002 |
| 3 | 50.002 | 0.003 |
| 4 | 49.924 | 0.005 |

Treatments 5 and 6 were prepared with two levels of molasses extract from Example 3 to give a carbohydrate load of 25 g (250 mL test solution). Eleven (11) samples were prepared per formulation: ten (10) for GI testing; and one (1) retained by QDPI&F.

| Treatment | High Pol Sucrose | Standard deviation | Polyphenol (Average weight) | Standard deviation |
|---|---|---|---|---|
| 5 | 25.254 | 0.003 | 4.975 | 0.022 |
| 6 | 25.253 | 0.004 | 9.986 | 0.025 |

The carbohydrate loads in these treatments are shown below.

| Treatment | Carbohydrate load (average) | Standard deviation |
|---|---|---|
| 5 | 25.004 | 0.003 |
| 6 | 25.002 | 0.004 |

Controls & Ingredients

| Product | Formulation | Notes |
|---|---|---|
| Glucose control | 100% glucose (glucodin) 10 × 50 g samples | Supplied by Sydney Uni |
| High Pol Sucrose | 98.88% sucrose 0.07% glucose 0.07% fructose 10 × 50 g samples | Sucrose supplied by MCM |
| Low Pol Sucrose | 88.5% sucrose 1.42% glucose 1.55% fructose 10 × 50 g samples | Sucrose supplied by MCM |
| Galactose | 10 g galactose | Galactose supplied by DPI&F |

Glycemic Index (GI) Test Methods

This study was conducted by the Human Nutrition Unit at the University of Sydney using internationally recognised GI methodology, which has been validated by results obtained from small experimental studies and large multi-centre research trials. The experimental procedures used in this study were in accordance with international standards for conducting ethical research with humans and were approved by the Human Research Ethics Committee of Sydney University.

Experimental Procedures

Using standard methodology to determine a food's GI value, a portion of the food containing between 10 and 50 grams of available carbohydrate is fed to 10 healthy people the morning after they have fasted for 10-12 hours overnight. A fasting blood sample is first obtained from each person and then the food is consumed, after which additional blood samples are obtained at regular intervals during the next two hours. In this way, it's possible to measure the total increase in blood sugar produced by that food over a two-hour period. The two-hour blood glucose (glycaemic) response for this test food is then compared to the two-hour blood glucose response produced by the same amount of carbohydrate in the form of pure glucose sugar (the reference food: GI value of glucose=100%). Therefore, GI values for foods and drinks are relative measures (ie. they indicate how high blood sugar levels rise after eating a particular food compared to the very high blood sugar response produced by the same amount of carbohydrate in the form of glucose sugar). Equal-carbohydrate portions of test foods and the reference food are used in GI experiments, because carbohydrate is the main component in food that causes the blood's glucose level to rise.

The night before each test session, the subjects ate a regular low-fat evening meal based on a carbohydrate-rich food, other than legumes, and then fasted for at least 10 hours overnight. The subjects were also required to avoid alcohol and unusual levels of food intake and physical activity for the whole day before each test session.

The next morning, the subjects reported to the research centre in a fasting condition. On arrival, the investigators first checked that the subjects were well and had complied with all of the preceding experimental conditions. The subjects then warmed a hand in hot water for one minute, after which two fasting finger-prick blood samples (−5 and 0 minutes) were obtained (a few drops of blood; sampled twice) using an automatic, non-reusable lancet device (Safe-T-Pro®, Boehringer Mannheim Gmbh, Mannheim, Germany). After the second fasting blood sample (0 minutes) was obtained, the subjects were seated at a table and given a fixed portion of the reference food or the test food, which they consumed together with 250 grams of plain water at a comfortable pace within 12 minutes. A stopwatch was started for each subject as soon as they started eating. The subjects were required to remain at the research centre for the next two hours during which additional blood samples were collected at 15, 30, 45, 60, 90 and 120 minutes after eating had commenced. Therefore, a total of eight blood samples were collected from each subject during each two-hour test session.

Measurement of the Subjects' Blood Glucose Responses

For each subject, the concentration of glucose in each of the eight whole blood samples collected from them during each test session was analysed in duplicate using a HemoCue® B-glucose photometric analyser employing a glucose dehydrogenase/mutarotase enzymatic assay (HemoCue AB, Ängelholm, Sweden). Each blood sample was collected into a plastic HemoCue® cuvette containing the enzymes and reagents for the blood glucose assay and then placed into the HemoCue analyser while the enzymatic reaction took place. Therefore, each blood sample was analysed immediately after it was collected.

For each of the 10 subjects, a two-hour blood glucose response curve was constructed for each of their test sessions using the average blood glucose concentrations for each of their eight blood samples. The two fasting blood samples were averaged to provide one baseline glucose concentration. The area under each two-hour blood glucose response curve (AUC) was then calculated in order to obtain a single number, which indicates the total increase in blood glucose during the two-hour test period in that subject as a result of ingesting that food. A glycaemic index (GI) value for each test sugar was then calculated for each subject by dividing their two-hour blood glucose AUC value for the test food by their average two-hour blood glucose AUC value for the reference food and multiplying by 100 to obtain a percentage score.

$$GI \text{ value for test food } (\%) = \frac{\text{Blood glucose } AUC \text{ value for the test food}}{\text{Average } AUC \text{ value for the equal carbohydrate portion of the reference food}} * 100$$

Due to differences in body weight and metabolism, blood glucose responses to the same food or drink can vary between different people. The use of the reference food to calculate GI values reduces the variation between the subjects' blood glucose results to the same food arising from these natural differences. Therefore, the GI value for the same food varies less between the subjects than their glucose AUC values for this food.

TABLE 18

The mean ± SEM GI values for the test foods and the reference food tested using a 50-gram equal carbohydrate portion (n = 9).

| Test Food | GI value (%) | GI category |
|---|---|---|
| Treatment 1 | 53 ± 5 | Low GI |
| Treatment 2 | 69 ± 5 | Moderate GI |
| Glucose - Reference Food | 100 ± 0 | High GI |

TABLE 19

The mean ± SEM GI values for the test foods and the reference food tested using a 50-gram equal carbohydrate portion (n = 9).

| Test Food | GI value (%) | GI category |
|---|---|---|
| Treatment 4 | 55 ± 7 | Low GI |
| Treatment 2 | 69 ± 5 | Moderate GI |
| Glucose - Reference Food | 100 ± 0 | High GI |

TABLE 20

The mean ± SEM GI values for the two test foods and the reference food tested using a 25-gram equal carbohydrate portion (n = 9).

| Test Food | GI value (%) | GI category |
|---|---|---|
| Treatment 6 | 51 ± 6 | Low GI |
| Treatment 5 | 58 ± 6 | Moderate GI |
| Glucose - Reference food | 100 ± 0 | High GI |

CONCLUSIONS

The results show that the various sweeteners of the invention have a low GI. In particular, the use of a complex carbohydrate such as galactose when added to sugar reduces the GI to a low level. Further, the use of a molasses extract will also reduce the GI of sugar to a low level. The word 'comprising' and forms of the word 'comprising' as used in this description and in the claims does not limit the invention claimed to exclude any variants or additions. Modifications and improvements to the invention will be readily apparent to those skilled in the art. Such modifications and improvements are intended to be within the scope of this invention.

The claims defining the invention are as follows:

1. A low GI sweetener suitable for human consumption, the sweetener consisting essentially of:
   (a) a sugar base that is at least 97% by weight sucrose; combined with
   (b) an amount of a GI lowering extract from a sugar processing product that is effective to lower the GI of the sugar base,
   the sugar processing product being selected from the group consisting of molasses, sugar mud, juice collected from a clarifying tank, foam collected from a clarifying tank, sugar cane field trash, sugar beet field trash, fibrated sugar cane tops, bagasse, sugar beet pulp, a sugar waste processing stream, and combinations of these,
   the sweetener having a GI no greater than 54.

2. The sweetener of claim 1, wherein the sugar processing product is molasses.

3. The sweetener of claim 2, wherein the molasses is sugar cane molasses.

4. The sweetener of claim 3, wherein the extract comprises a polyphenol.

5. The sweetener of claim 3, wherein the extract comprises an organic acid selected from the group consisting of trans-aconitic acid, oxalic, cis-aconitic, citric, phosphoric, gluconic, malic, succinic, lactic, formic and acetic acids and mixtures of these.

6. The sweetener of claim 5, wherein the organic acid is selected from the group consisting of cis-aconitic, citric, phosphoric, gluconic, malic, trans-aconitic, succinic, and lactic acids and mixtures of these.

7. The sweetener of claim 5, wherein the extract also comprises a polyphenol.

8. A food product comprising the sweetener of claim 1.

9. The food product of claim 8, being a beverage.

10. The sweetener of claim 1, wherein the sugar base comprises at least 99% by weight sucrose.

11. A food product comprising a known sweetener, wherein the improvement comprises the sweetener of claim 1 being present in place of at least a portion of the known sweetener.

12. A method for producing a food product, wherein the improvement comprises replacing a sweetener previously used in the food product with the sweetener of claim 1.

* * * * *